US011866786B2

United States Patent
(12) United States Patent
Frumkin et al.

(10) Patent No.: US 11,866,786 B2
(45) Date of Patent: Jan. 9, 2024

(54) KITS AND METHODS FOR DIAGNOSING LUNG CANCER

(71) Applicant: NUCLEIX LTD., Rehovot (IL)

(72) Inventors: Danny Frumkin, Rehovot (IL); Adam Wasserstrom, Ness Ziona (IL)

(73) Assignee: NUCLEIX LTD., Rehovot (IL)

( * ) Notice: Subject to any disclaimer, the term of this patent is extended or adjusted under 35 U.S.C. 154(b) by 0 days.

(21) Appl. No.: 16/962,293

(22) PCT Filed: Jan. 17, 2019

(86) PCT No.: PCT/IL2019/050071
§ 371 (c)(1),
(2) Date: Jul. 15, 2020

(87) PCT Pub. No.: WO2019/142193
PCT Pub. Date: Jul. 25, 2019

(65) Prior Publication Data
US 2020/0370131 A1 Nov. 26, 2020

Related U.S. Application Data

(60) Provisional application No. 62/618,649, filed on Jan. 18, 2018.

(51) Int. Cl.
*C12Q 1/6886* (2018.01)
*C12Q 1/686* (2018.01)

(52) U.S. Cl.
CPC ........... *C12Q 1/6886* (2013.01); *C12Q 1/686* (2013.01); *C12Q 2521/331* (2013.01); *C12Q 2561/113* (2013.01); *C12Q 2600/112* (2013.01); *C12Q 2600/154* (2013.01)

(58) Field of Classification Search
CPC ........................ C12Q 1/6886; C12Q 2600/154
See application file for complete search history.

(56) References Cited

U.S. PATENT DOCUMENTS 8,399,193 B2 * 3/2013 Pfeifer ................ C12Q 1/6886 435/6.11
9,476,100 B1 10/2016 Frumkin

FOREIGN PATENT DOCUMENTS

WO 2011001274 A2 1/2011
WO 2011070441 A2 6/2011
WO 2013055530 A1 4/2013
WO 2017006317 A1 1/2017

OTHER PUBLICATIONS

Ellinger, J. et al. The Journal of Urology 182:324-329 (Jul. 2009). (Year: 2009).*
Liloglou et al., (2014) Epigenetic biomarkers in lung cancer. Cancer Lett 342(2): 200-212.
Lu et al., (2017) Methylated DNA/RNA in Body Fluids as Biomarkers for Lung Cancer. Biol Proced Online 19: 2; 9 pages.
(Continued)

*Primary Examiner* — Diana B Johannsen
(74) *Attorney, Agent, or Firm* — Acuity Law Group, PC; Michael A. Whittaker

(57) ABSTRACT

Methods and kits for identification of lung cancer in a subject based on alterations in DNA methylation at selected genomic loci are provided.

9 Claims, 2 Drawing Sheets

Specification includes a Sequence Listing.

(56) References Cited

OTHER PUBLICATIONS

Um et al., (2017) Bronchial biopsy specimen as a surrogate for DNA methylation analysis in inoperable lung cancer. Clin Epigenetics 9: 131; 10 pages.
Anagnostou et al., (2019) Dynamics of Tumor and Immune Responses during Immune Checkpoint Blockade in Non-Small Cell Lung Cancer. Cancer Res 79(6): 1214-1225.
Brahmer et al., (2018) The Society for Immunotherapy of Cancer consensus statement on immunotherapy for the treatment of non-small cell lung cancer (Nsclc). J Immunother Cancer 6(1): 75; 15 pages.
Burdett et al., (2011) Pre operative chemotherapy improves survival and reduces recurrence in operable non-small cell lung cancer: Preliminary results of a systematic review and meta-analysis of individual patient data from 13 randomised trials. Journal of Thoracic Oncology 6(Suppl 2): 374-375.
Cascone et al., (2018) A phase I study of neoadjuvant cisplatin (C), docetaxel (D) and nintedanib (N) for resectable non-small cell lung cancer (NSCLC). J Clin Oncol 36(15 suppl): abstr 8555.
Cascone et al., (2018) Induction Cisplatin Docetaxel Followed by Surgery and Erlotinib in Non-Small Cell Lung Cancer. Ann Thorac Surg 105(2): 418-424.
Chen et al., (2014) Cancer-associated fibroblasts regulate the plasticity of lung cancer stemness via paracrine signalling. Nat Commun 5: 3472; 17 pages.
Cottrell et al., (2018) Pathologic features of response to neoadjuvant anti-PD-1 in resected non-small-cell lung carcinoma: a proposal for quantitative immune-related pathologic response criteria (irPRC). Ann Oncol 29(8): 1853-1860.
Ehrich et al., (2006) Cytosine methylation profiles as a molecular marker in non-small cell lung cancer. Cancer Res 66(22): 10911-10918.
Forde et al., (2018) Neoadjuvant PD-1 Blockade in Resectable Lung Cancer N Engl J Med 378(21): 1976-1986 with correction.
Heller et al., (2010) Lung cancer: from single-gene methylation to methylome profiling. Cancer Metastasis Rev 29(1): 95-107.
Kim et al., (2019) Combined genomic and epigenomic assessment of cell-free circulating tumor DNA (ctDNA) improves assay sensitivity in early-stage colorectal cancer (CRC) [abstract]. In: Proceedings of the American Association for Cancer Research Annual Meeting Mar. 29-Apr. 3, 2019; Atlanta, GA. Philadelphia (PA): AACR; Cancer Res 79(13 Suppl): Abstract nr 916.
Lam et al., (2018) Circulating tumor DNA analysis with a novel variant classifier for recurrence detection in resected, early-stage lung cancer. Journal of Thoracic Oncology 13(10S): S438.
Leng et al., (2012) Defining a gene promoter methylation signature in sputum for lung cancer risk assessment. Clin Cancer Res 18(12): 3387-3395.
NSCLC Meta-analysis Collaborative Group (2014) Preoperative chemotherapy for non-small-cell lung cancer: a systematic review and meta-analysis of individual participant data. Lancet 383(9928): 1561-1571.
Parra et al., (2018) Effect of neoadjuvant chemotherapy on the immune microenvironment in non-small cell lung carcinomas as determined by multiplex immunofluorescence and image analysis approaches. J Immunother Cancer 6(1): 48; 11 pages.
Pataer et al., (2012) Histopathologic response criteria predict survival of patients with resected lung cancer after neoadjuvant chemotherapy. J Thorac Oncol 7(5): 825-832.
Pignon et al., (2008) Lung adjuvant cisplatin evaluation: a pooled analysis by the LACE Collaborative Group. J Clin Oncol 26(21): 3552-3559.
Pisters et al., (2010) Surgery with or without preoperative paclitaxel and carboplatin in early-stage non-small-cell lung cancer: Southwest Oncology Group Trial S9900, an intergroup, randomized, phase III trial. J Clin Oncol 28(11): 1843-1849.
Qu et al., (2019) Pathologic Assessment After Neoadjuvant Chemotherapy for NSCLC: Importance and Implications of Distinguishing Adenocarcinoma From Squamous Cell Carcinoma. J Thorac Oncol 14(3): 482-493.
Rauch et al., (2008) High-resolution mapping of DNA hypermethylation and hypomethylation in lung cancer. Proc Natl Acad Sci U S A 105(1): 252-257.
Vaissière et al., (2009) Quantitative analysis of DNA methylation profiles in lung cancer identifies aberrant DNA methylation of specific genes and its association with gender and cancer risk factors. Cancer Res 69(1): 243-252.
Weissferdt et al., (2020) Agreement on Major Pathological Response in NSCLC Patients Receiving Neoadjuvant Chemotherapy. Clin Lung Cancer 21(4): 341-348.
Anglim et al., Identification of a panel of sensitive and specific DNA methylation markers for squamous cell lung cancer. Mol Cancer. Jul. 10, 2008;7:62 (13 pages total).
Wielscher et al., Diagnostic Performance of Plasma DNA Methylation Profiles in Lung Cancer, Pulmonary Fibrosis and COPD. EBioMedicine Jul. 2, 2015;2(8): 929-936.

* cited by examiner

SEQUENCE LISTING

<160> NUMBER OF SEQ ID NOS: 91

<210> SEQ ID NO 1
<211> LENGTH: 85
<212> TYPE: DNA
<213> ORGANISM: Homo sapiens

<400> SEQUENCE: 1
agtagcgccc actgagcggt ttttcagttg ctgcaccgtt cttagcgccc aacggaacgt 60
ttcccgtacg cggagtccat aagtt 85

<210> SEQ ID NO 2
<211> LENGTH: 69
<212> TYPE: DNA
<213> ORGANISM: Homo sapiens

<400> SEQUENCE: 2
cggtcccgca gcgcccgcca cacacccgcg ccagaggtcc agcgcatgtg cagtgaaatg 60
gcctagccc 69

<210> SEQ ID NO 3
<211> LENGTH: 72
<212> TYPE: DNA
<213> ORGANISM: Homo sapiens

<400> SEQUENCE: 3
cggatagcgc ggcgggcgac agccccccgg ataaccccgc cgagggaggg gcgcttgtaa 60
aaccgagcgg cg 72

<210> SEQ ID NO 4
<211> LENGTH: 60
<212> TYPE: DNA
<213> ORGANISM: Homo sapiens

<400> SEQUENCE: 4
tcctccttgc cttctttcgc cgaaaggggg cgcgctcctc ccaggctgcg ctggtaccta 60

<210> SEQ ID NO 5
<211> LENGTH: 78
<212> TYPE: DNA
<213> ORGANISM: Homo sapiens

<400> SEQUENCE: 5
aggacccgct ccgcaaagcg cccaccctcg agggaggaaa gccgagctgc gcctccgcgc 60
aaggccaggg agtgtggc 78

<210> SEQ ID NO 6
<211> LENGTH: 73
<212> TYPE: DNA
<213> ORGANISM: Homo sapiens

<400> SEQUENCE: 6
aggccgcgag cgcggcgcga tcagtagcgc ccactaacag ttcgttctgc acggcggagc 60
gcgagaccgc gga 73

<210> SEQ ID NO 7
<211> LENGTH: 60
<212> TYPE: DNA
<213> ORGANISM: Homo sapiens

<400> SEQUENCE: 7
agactaactt ttctcttgta cagaatcatc aggctaaatt tttggcatta tttcagtcct 60

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
tgcattctct caggagctgg 20

<210> SEQ ID NO 9
<211> LENGTH: 19
<212> TYPE: DNA
<213> ORGANISM: Artificial Sequence
<220> FEATURE:
<223> OTHER INFORMATION: Primer

<400> SEQUENCE: 9
gagccaagct cggtctccg 19

<210> SEQ ID NO 10
<211> LENGTH: 21
<212> TYPE: DNA
<213> ORGANISM: Artificial Sequence
<220> FEATURE:
<223> OTHER INFORMATION: Primer

<400> SEQUENCE: 10
cagcaacgct tttgccagta g 21

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
tctaatgcgg agctggcggt 20

<210> SEQ ID NO 12
<211> LENGTH: 21
<212> TYPE: DNA
<213> ORGANISM: Artificial Sequence
<220> FEATURE:
<223> OTHER INFORMATION: Primer

<400> SEQUENCE: 12
cccactgagc ggtttttcag t 21

<210> SEQ ID NO 13
<211> LENGTH: 20
<212> TYPE: DNA
<213> ORGANISM: Artificial Sequence
<220> FEATURE:
<223> OTHER INFORMATION: Primer

<400> SEQUENCE: 13
cgtttcccgt acgcggagtc 20

<210> SEQ ID NO 14
<211> LENGTH: 20
<212> TYPE: DNA
<213> ORGANISM: Artificial Sequence
<220> FEATURE:
<223> OTHER INFORMATION: Primer

<400> SEQUENCE: 14
gttttaatgt gttgtgacag 20

<210> SEQ ID NO 15
<211> LENGTH: 20
<212> TYPE: DNA
<213> ORGANISM: Artificial Sequence
<220> FEATURE:
<223> OTHER INFORMATION: Primer

<400> SEQUENCE: 15
gtgctgctag aaagaaactg 20

<210> SEQ ID NO 16
<211> LENGTH: 21
<212> TYPE: DNA
<213> ORGANISM: Artificial Sequence
<220> FEATURE:
<223> OTHER INFORMATION: Primer

<400> SEQUENCE: 16
gggtttagga agttcctagg a 21

<210> SEQ ID NO 17
<211> LENGTH: 20
<212> TYPE: DNA
<213> ORGANISM: Artificial Sequence
<220> FEATURE:
<223> OTHER INFORMATION: Primer

<400> SEQUENCE: 17
tactagttgg cacagaggct 20

<210> SEQ ID NO 18
<211> LENGTH: 20
<212> TYPE: DNA
<213> ORGANISM: Artificial Sequence
<220> FEATURE:
<223> OTHER INFORMATION: Primer

<400> SEQUENCE: 18
cggtgccaga accgagaaag 20

<210> SEQ ID NO 19
<211> LENGTH: 20
<212> TYPE: DNA
<213> ORGANISM: Artificial Sequence
<220> FEATURE:
<223> OTHER INFORMATION: Primer

<400> SEQUENCE: 19
accgttctgc accgtaaaac 20

<210> SEQ ID NO 20
<211> LENGTH: 20
<212> TYPE: DNA
<213> ORGANISM: Artificial Sequence
<220> FEATURE:
<223> OTHER INFORMATION: Primer

<400> SEQUENCE: 20
cggaataggg tttgcaaatc 20

<210> SEQ ID NO 21
<211> LENGTH: 20
<212> TYPE: DNA
<213> ORGANISM: Artificial Sequence
<220> FEATURE:
<223> OTHER INFORMATION: Primer

<400> SEQUENCE: 21
aggagatgct gcttgttcgg 20

<210> SEQ ID NO 22
<211> LENGTH: 20
<212> TYPE: DNA
<213> ORGANISM: Artificial Sequence
<220> FEATURE:
<223> OTHER INFORMATION: Primer

<400> SEQUENCE: 22
gttgaagctt ttaatacatg 20

<210> SEQ ID NO 23
<211> LENGTH: 19
<212> TYPE: DNA
<213> ORGANISM: Artificial Sequence
<220> FEATURE:
<223> OTHER INFORMATION: Primer

<400> SEQUENCE: 23
acagctcacg gtcccgcag 19

<210> SEQ ID NO 24
<211> LENGTH: 17
<212> TYPE: DNA
<213> ORGANISM: Artificial Sequence
<220> FEATURE:
<223> OTHER INFORMATION: Primer

<400> SEQUENCE: 24
gcccgccaca cacccgc 17

<210> SEQ ID NO 25
<211> LENGTH: 21
<212> TYPE: DNA
<213> ORGANISM: Artificial Sequence
<220> FEATURE:
<223> OTHER INFORMATION: Primer

<400> SEQUENCE: 25
cttgagatga ggttcccaag c 21

<210> SEQ ID NO 26
<211> LENGTH: 21
<212> TYPE: DNA
<213> ORGANISM: Artificial Sequence
<220> FEATURE:
<223> OTHER INFORMATION: Primer

<400> SEQUENCE: 26
agatgagtag cgagccttgt c 21

<210> SEQ ID NO 27
<211> LENGTH: 21
<212> TYPE: DNA
<213> ORGANISM: Artificial Sequence
<220> FEATURE:
<223> OTHER INFORMATION: Primer

<400> SEQUENCE: 27
cgtgctttgc cgatcgaatt c 21

<210> SEQ ID NO 28
<211> LENGTH: 20
<212> TYPE: DNA
<213> ORGANISM: Artificial Sequence
<220> FEATURE:
<223> OTHER INFORMATION: Primer

<400> SEQUENCE: 28
ttcctgctcg agtccactcg 20

<210> SEQ ID NO 29
<211> LENGTH: 21
<212> TYPE: DNA
<213> ORGANISM: Artificial Sequence
<220> FEATURE:
<223> OTHER INFORMATION: Primer

<400> SEQUENCE: 29
cgggtgtatc ttcctgctcg a 21

<210> SEQ ID NO 30

<211> LENGTH: 20
<212> TYPE: DNA
<213> ORGANISM: Artificial Sequence
<220> FEATURE:
<223> OTHER INFORMATION: Primer

<400> SEQUENCE: 30
cgagccttga cggagggaga 20

<210> SEQ ID NO 31
<211> LENGTH: 20
<212> TYPE: DNA
<213> ORGANISM: Artificial Sequence
<220> FEATURE:
<223> OTHER INFORMATION: Primer

<400> SEQUENCE: 31
cggagggaga atggaaagat 20

<210> SEQ ID NO 32
<211> LENGTH: 20
<212> TYPE: DNA
<213> ORGANISM: Artificial Sequence
<220> FEATURE:
<223> OTHER INFORMATION: Primer

<400> SEQUENCE: 32
tttcctccgc caccgagtag 20

<210> SEQ ID NO 33
<211> LENGTH: 21
<212> TYPE: DNA
<213> ORGANISM: Artificial Sequence
<220> FEATURE:
<223> OTHER INFORMATION: Primer

<400> SEQUENCE: 33
gaagtttaag tttccaggtc c 21

<210> SEQ ID NO 34
<211> LENGTH: 21
<212> TYPE: DNA
<213> ORGANISM: Artificial Sequence
<220> FEATURE:
<223> OTHER INFORMATION: Primer

<400> SEQUENCE: 34
atttgcgaag tttaagtttc c 21

<210> SEQ ID NO 35
<211> LENGTH: 20
<212> TYPE: DNA
<213> ORGANISM: Artificial Sequence
<220> FEATURE:
<223> OTHER INFORMATION: Primer

<400> SEQUENCE: 35
agcagccagg gatcggatag 20

<210> SEQ ID NO 36
<211> LENGTH: 20
<212> TYPE: DNA
<213> ORGANISM: Artificial Sequence
<220> FEATURE:
<223> OTHER INFORMATION: Primer

<400> SEQUENCE: 36
tcggcagccg ccctggtagc 20

<210> SEQ ID NO 37
<211> LENGTH: 20
<212> TYPE: DNA
<213> ORGANISM: Artificial Sequence
<220> FEATURE:
<223> OTHER INFORMATION: Primer

<400> SEQUENCE: 37
ccccatttgc gaagtttaag 20

<210> SEQ ID NO 38
<211> LENGTH: 20
<212> TYPE: DNA
<213> ORGANISM: Artificial Sequence
<220> FEATURE:
<223> OTHER INFORMATION: Primer

<400> SEQUENCE: 38
ggcagtctaa tccttaattt 20

<210> SEQ ID NO 39
<211> LENGTH: 20
<212> TYPE: DNA
<213> ORGANISM: Artificial Sequence
<220> FEATURE:
<223> OTHER INFORMATION: Primer

<400> SEQUENCE: 39
attttaataa tcaggataaa 20

<210> SEQ ID NO 40
<211> LENGTH: 21
<212> TYPE: DNA
<213> ORGANISM: Artificial Sequence
<220> FEATURE:
<223> OTHER INFORMATION: Primer

<400> SEQUENCE: 40
atgttcgagt cggtcgtaac g 21

<210> SEQ ID NO 41
<211> LENGTH: 23
<212> TYPE: DNA
<213> ORGANISM: Artificial Sequence
<220> FEATURE:
<223> OTHER INFORMATION: Primer

<400> SEQUENCE: 41
gtacacaaac gaatactagc taa 23

<210> SEQ ID NO 42
<211> LENGTH: 21
<212> TYPE: DNA
<213> ORGANISM: Artificial Sequence
<220> FEATURE:
<223> OTHER INFORMATION: Primer

<400> SEQUENCE: 42
ctaggcagtc taatccttaa t 21

<210> SEQ ID NO 43
<211> LENGTH: 21
<212> TYPE: DNA

<213> ORGANISM: Artificial Sequence
<220> FEATURE:
<223> OTHER INFORMATION: Primer

<400> SEQUENCE: 43
atactagcta aggccgatga t 21

<210> SEQ ID NO 44
<211> LENGTH: 21
<212> TYPE: DNA
<213> ORGANISM: Artificial Sequence
<220> FEATURE:
<223> OTHER INFORMATION: Primer

<400> SEQUENCE: 44
ctctctgctg tagcgacgcc a 21

<210> SEQ ID NO 45
<211> LENGTH: 21
<212> TYPE: DNA
<213> ORGANISM: Artificial Sequence
<220> FEATURE:
<223> OTHER INFORMATION: Primer

<400> SEQUENCE: 45
gctttccgcc gggtaaatta g 21

<210> SEQ ID NO 46
<211> LENGTH: 22
<212> TYPE: DNA
<213> ORGANISM: Artificial Sequence
<220> FEATURE:
<223> OTHER INFORMATION: Primer

<400> SEQUENCE: 46
tttggttata gtggtgtggt ct 22

<210> SEQ ID NO 47
<211> LENGTH: 21
<212> TYPE: DNA
<213> ORGANISM: Artificial Sequence
<220> FEATURE:
<223> OTHER INFORMATION: Primer

<400> SEQUENCE: 47
ccaccccatc ttcgcagttc t 21

<210> SEQ ID NO 48
<211> LENGTH: 20
<212> TYPE: DNA
<213> ORGANISM: Artificial Sequence
<220> FEATURE:
<223> OTHER INFORMATION: Primer

<400> SEQUENCE: 48
tcctccttgc cttctttcgc 20

<210> SEQ ID NO 49
<211> LENGTH: 22
<212> TYPE: DNA
<213> ORGANISM: Artificial Sequence
<220> FEATURE:
<223> OTHER INFORMATION: Primer

<400> SEQUENCE: 49
atagtggtgt ggtctctgcc tc 22

<210> SEQ ID NO 50
<211> LENGTH: 20
<212> TYPE: DNA
<213> ORGANISM: Artificial Sequence
<220> FEATURE:
<223> OTHER INFORMATION: Primer

<400> SEQUENCE: 50
gttttgttac tgtctgtcct 20

<210> SEQ ID NO 51
<211> LENGTH: 21
<212> TYPE: DNA
<213> ORGANISM: Artificial Sequence
<220> FEATURE:
<223> OTHER INFORMATION: Primer

<400> SEQUENCE: 51
tcctgccagg tgtctacatg t 21

<210> SEQ ID NO 52
<211> LENGTH: 22
<212> TYPE: DNA
<213> ORGANISM: Artificial Sequence
<220> FEATURE:
<223> OTHER INFORMATION: Primer

<400> SEQUENCE: 52
actgtctgtc ctgcaggaac cc 22

<210> SEQ ID NO 53
<211> LENGTH: 21
<212> TYPE: DNA
<213> ORGANISM: Artificial Sequence
<220> FEATURE:
<223> OTHER INFORMATION: Primer

<400> SEQUENCE: 53
tgaaggcagg ataggtacca g 21

<210> SEQ ID NO 54
<211> LENGTH: 22
<212> TYPE: DNA
<213> ORGANISM: Artificial Sequence
<220> FEATURE:
<223> OTHER INFORMATION: Primer

<400> SEQUENCE: 54
tcaaactatt atttcccacg tt 22

<210> SEQ ID NO 55
<211> LENGTH: 20
<212> TYPE: DNA
<213> ORGANISM: Artificial Sequence
<220> FEATURE:
<223> OTHER INFORMATION: Primer

<400> SEQUENCE: 55
acatgtttcc attaagatgc 20

<210> SEQ ID NO 56
<211> LENGTH: 21
<212> TYPE: DNA
<213> ORGANISM: Artificial Sequence
<220> FEATURE:

<223> OTHER INFORMATION: Primer

<400> SEQUENCE: 56
cctgacgttc ctggaatatg c 21

<210> SEQ ID NO 57
<211> LENGTH: 21
<212> TYPE: DNA
<213> ORGANISM: Artificial Sequence
<220> FEATURE:
<223> OTHER INFORMATION: Primer

<400> SEQUENCE: 57
gcaatgactt cttttaggac a 21

<210> SEQ ID NO 58
<211> LENGTH: 20
<212> TYPE: DNA
<213> ORGANISM: Artificial Sequence
<220> FEATURE:
<223> OTHER INFORMATION: Primer

<400> SEQUENCE: 58
tgaaagcagc attaaccgtg 20

<210> SEQ ID NO 59
<211> LENGTH: 19
<212> TYPE: DNA
<213> ORGANISM: Artificial Sequence
<220> FEATURE:
<223> OTHER INFORMATION: Primer

<400> SEQUENCE: 59
aggacccgct ccgcaaagc 19

<210> SEQ ID NO 60
<211> LENGTH: 20
<212> TYPE: DNA
<213> ORGANISM: Artificial Sequence
<220> FEATURE:
<223> OTHER INFORMATION: Primer

<400> SEQUENCE: 60
accctcgagg gaggaaagcc 20

<210> SEQ ID NO 61
<211> LENGTH: 21
<212> TYPE: DNA
<213> ORGANISM: Artificial Sequence
<220> FEATURE:
<223> OTHER INFORMATION: Primer

<400> SEQUENCE: 61
aacccgttac tttccaagga c 21

<210> SEQ ID NO 62
<211> LENGTH: 19
<212> TYPE: DNA
<213> ORGANISM: Artificial Sequence
<220> FEATURE:
<223> OTHER INFORMATION: Primer

<400> SEQUENCE: 62
gccacactcc ctggccttg 19

<210> SEQ ID NO 63
<211> LENGTH: 19
<212> TYPE: DNA
<213> ORGANISM: Artificial Sequence
<220> FEATURE:
<223> OTHER INFORMATION: Primer

<400> SEQUENCE: 63
gcggggctcg agccacact 19

<210> SEQ ID NO 64
<211> LENGTH: 19
<212> TYPE: DNA
<213> ORGANISM: Artificial Sequence
<220> FEATURE:
<223> OTHER INFORMATION: Primer

<400> SEQUENCE: 64
cctccgcact gggaggctg 19

<210> SEQ ID NO 65
<211> LENGTH: 19
<212> TYPE: DNA
<213> ORGANISM: Artificial Sequence
<220> FEATURE:
<223> OTHER INFORMATION: Primer

<400> SEQUENCE: 65
tcgcagccga ggcaggtct 19

<210> SEQ ID NO 66
<211> LENGTH: 22
<212> TYPE: DNA
<213> ORGANISM: Artificial Sequence
<220> FEATURE:
<223> OTHER INFORMATION: Primer

<400> SEQUENCE: 66
cccgacagtg tcattgatta ac 22

<210> SEQ ID NO 67
<211> LENGTH: 20
<212> TYPE: DNA
<213> ORGANISM: Artificial Sequence
<220> FEATURE:
<223> OTHER INFORMATION: Primer

<400> SEQUENCE: 67
cctccgcagc tgggaggctg 20

<210> SEQ ID NO 68
<211> LENGTH: 20
<212> TYPE: DNA
<213> ORGANISM: Artificial Sequence
<220> FEATURE:
<223> OTHER INFORMATION: Primer

<400> SEQUENCE: 68
ctcggggact gctactttgc 20

<210> SEQ ID NO 69
<211> LENGTH: 20
<212> TYPE: DNA
<213> ORGANISM: Artificial Sequence
<220> FEATURE:
<223> OTHER INFORMATION: Primer

<400> SEQUENCE: 69
ggtcaagtgt cacgtcctcc 20

<210> SEQ ID NO 70
<211> LENGTH: 23
<212> TYPE: DNA
<213> ORGANISM: Artificial Sequence
<220> FEATURE:
<223> OTHER INFORMATION: Primer

<400> SEQUENCE: 70
atattcctgt aatgtattta aat 23

<210> SEQ ID NO 71
<211> LENGTH: 19
<212> TYPE: DNA
<213> ORGANISM: Artificial Sequence
<220> FEATURE:
<223> OTHER INFORMATION: Primer

<400> SEQUENCE: 71
tacgcggggc cgtgtgaat 19

<210> SEQ ID NO 72
<211> LENGTH: 20
<212> TYPE: DNA
<213> ORGANISM: Artificial Sequence
<220> FEATURE:
<223> OTHER INFORMATION: Primer

<400> SEQUENCE: 72
ggtcaagtgt cacgtcctcc 20

<210> SEQ ID NO 73
<211> LENGTH: 20
<212> TYPE: DNA
<213> ORGANISM: Artificial Sequence
<220> FEATURE:
<223> OTHER INFORMATION: Primer

<400> SEQUENCE: 73
aagtgtcacg tcctccgcaa 20

<210> SEQ ID NO 74
<211> LENGTH: 20
<212> TYPE: DNA
<213> ORGANISM: Artificial Sequence
<220> FEATURE:
<223> OTHER INFORMATION: Primer

<400> SEQUENCE: 74
gcgaggacgc aaacaccatt 20

<210> SEQ ID NO 75
<211> LENGTH: 20
<212> TYPE: DNA
<213> ORGANISM: Artificial Sequence
<220> FEATURE:
<223> OTHER INFORMATION: Primer

<400> SEQUENCE: 75
cctaaaggac cctaccaagc 20

<210> SEQ ID NO 76
<211> LENGTH: 21

<212> TYPE: DNA
<213> ORGANISM: Artificial Sequence
<220> FEATURE:
<223> OTHER INFORMATION: Primer

<400> SEQUENCE: 76
gtgcctgaac tcttcctcct t 21

<210> SEQ ID NO 77
<211> LENGTH: 19
<212> TYPE: DNA
<213> ORGANISM: Artificial Sequence
<220> FEATURE:
<223> OTHER INFORMATION: Primer

<400> SEQUENCE: 77
ttccgtgggt ccgcggtct 19

<210> SEQ ID NO 78
<211> LENGTH: 21
<212> TYPE: DNA
<213> ORGANISM: Artificial Sequence
<220> FEATURE:
<223> OTHER INFORMATION: Primer

<400> SEQUENCE: 78
atcagaaaga ccattaggat c 21

<210> SEQ ID NO 79
<211> LENGTH: 21
<212> TYPE: DNA
<213> ORGANISM: Artificial Sequence
<220> FEATURE:
<223> OTHER INFORMATION: Primer

<400> SEQUENCE: 79
ccgaagggaa agaaaaatca g 21

<210> SEQ ID NO 80
<211> LENGTH: 23
<212> TYPE: DNA
<213> ORGANISM: Artificial Sequence
<220> FEATURE:
<223> OTHER INFORMATION: Primer

<400> SEQUENCE: 80
agcaaggtga agactaactt ttc 23

<210> SEQ ID NO 81
<211> LENGTH: 23
<212> TYPE: DNA
<213> ORGANISM: Artificial Sequence
<220> FEATURE:
<223> OTHER INFORMATION: Primer

<400> SEQUENCE: 81
cttgtacaga atcatcaggc taa 23

<210> SEQ ID NO 82
<211> LENGTH: 25
<212> TYPE: DNA
<213> ORGANISM: Artificial Sequence
<220> FEATURE:
<223> OTHER INFORMATION: Primer

<400> SEQUENCE: 82
gtccttggag acatctgaga gattc 25

<210> SEQ ID NO 83
<211> LENGTH: 20
<212> TYPE: DNA
<213> ORGANISM: Artificial Sequence
<220> FEATURE:
<223> OTHER INFORMATION: Primer

<400> SEQUENCE: 83
gacatctgag agattccggg 20

<210> SEQ ID NO 84
<211> LENGTH: 22
<212> TYPE: DNA
<213> ORGANISM: Artificial Sequence
<220> FEATURE:
<223> OTHER INFORMATION: Primer

<400> SEQUENCE: 84
caaagaaagc aaggtgaaga ct 22

<210> SEQ ID NO 85
<211> LENGTH: 24
<212> TYPE: DNA
<213> ORGANISM: Artificial Sequence
<220> FEATURE:
<223> OTHER INFORMATION: Primer

<400> SEQUENCE: 85
cagtccttgg agacatctga gaga 24

<210> SEQ ID NO 86
<211> LENGTH: 23
<212> TYPE: DNA
<213> ORGANISM: Artificial Sequence
<220> FEATURE:
<223> OTHER INFORMATION: Primer

<400> SEQUENCE: 86
tgaagtgaac tattccttag gtg 23

<210> SEQ ID NO 87
<211> LENGTH: 23
<212> TYPE: DNA
<213> ORGANISM: Artificial Sequence
<220> FEATURE:
<223> OTHER INFORMATION: Primer

<400> SEQUENCE: 87
gtctccaagg actgaaataa tgc 23

<210> SEQ ID NO 88
<211> LENGTH: 28
<212> TYPE: DNA
<213> ORGANISM: Artificial Sequence
<220> FEATURE:
<223> OTHER INFORMATION: Primer

<400> SEQUENCE: 88
gagtagcaaa aaatagctga agtgaact 28

<210> SEQ ID NO 89
<211> LENGTH: 23
<212> TYPE: DNA
<213> ORGANISM: Artificial Sequence

```
<220> FEATURE:
<223> OTHER INFORMATION: Primer

<400> SEQUENCE: 89

tgacaaccaa tgagtagcaa aaa                                              23


<210> SEQ ID NO 90
<211> LENGTH: 20
<212> TYPE: DNA
<213> ORGANISM: Artificial Sequence
<220> FEATURE:
<223> OTHER INFORMATION: Primer

<400> SEQUENCE: 90

gttgtcagtg tggccagaga                                                  20


<210> SEQ ID NO 91
<211> LENGTH: 21
<212> TYPE: DNA
<213> ORGANISM: Artificial Sequence
<220> FEATURE:
<223> OTHER INFORMATION: Primer

<400> SEQUENCE: 91

tgttgtcagt gtggccagag a                                                21
```

KITS AND METHODS FOR DIAGNOSING LUNG CANCER

FIELD OF THE INVENTION

The present invention relates to kits and methods for identifying lung cancer in a subject by analyzing a biological sample derived therefrom. More particularly, the present invention relates to identification of lung cancer by analyzing DNA from plasma samples. The methods are based on differences in DNA methylation between normal and lung cancer DNA.

BACKGROUND OF THE INVENTION

Lung cancer, a cancer arising from cells in the lungs, is one of the most common and serious types of cancer. There are two main types of lung cancer, namely, non-small cell lung cancer (NSCLC), which is the most common type, and small cell lung cancer. NSCLC has several subtypes, including squamous cell carcinoma, adenocarcinoma and large cell carcinoma.

The general prognosis of lung cancer is poor since lung cancer does not usually cause noticeable symptoms until it is spread through the lungs and sometimes also into other parts of the body. Efficient early detection methods can lead to improved outcomes, however there are no good screening methods for lung cancer which can be used for early diagnosis, especially prior to appearance of symptoms.

Three screening tests have been studied to determine whether they could reduce mortality from lung cancer: low-dose computed tomography (CT) scan of the chest, chest X-rays and sputum cytology. Among the tested methods, only low-dose CT screening for high risk individuals (heavy smokers) was shown to decrease lung cancer mortality. However, CT scans, even at low doses, expose the chest to radiation. In addition, the low-dose CT scan finds many abnormalities that turn out not to be cancer, but still have to be checked out with more CT scans and additional tests, some of which are invasive.

The definitive diagnosis of lung cancer is based on histological examination of a suspicious tissue following biopsy. The procedure involves bronchoscopy or CT-guided biopsy to sample the suspicious tissue.

WO 2011/001274 and WO 2011/070441, assigned to the Applicant of the present invention, disclose methods for identifying DNA from a natural source and methods for categorization of DNA samples into different types of tissue, respectively, based on signal ratios between specific genomic loci following amplification.

WO 2017/006317, assigned to the Applicant of the present invention, discloses methods and kits for identification of bladder cancer in a subject based on alterations in DNA methylation at selected genomic loci.

There is an unmet need for methods and kits for screening and diagnosing lung cancer in subjects in need thereof, which are non-invasive, do not require well-trained pathologists and characterized with high specificity and high sensitivity.

SUMMARY OF THE INVENTION

The present invention provides according to some aspects methods and kits for identification of lung cancer in subjects in need thereof by analyzing DNA from plasma samples. The methods and kits of the present invention are based on methylation differences at selected genomic loci between normal DNA and lung cancer DNA.

More particularly, the methods and kits of the present invention utilize a set of genomic loci that unexpectedly were found to be highly methylated in DNA from plasma samples of lung cancer patients, and not in DNA from plasma samples of healthy subjects. Thus, the set of genomic loci disclosed herein may be used for determining whether a given plasma sample is from a lung cancer patient or from a healthy subject.

According to the methods and kits of the present invention, DNA from a plasma sample of a tested subject is digested with at least one methylation-sensitive restriction enzyme that cleaves its recognition sequence only if it is unmethylated. The set of genomic loci disclosed herein, denoted "restriction loci", contain the recognition sequence of the at least one methylation-sensitive restriction enzyme and are therefore cut (digested) according to their methylation level, where higher methylation results in less digestion by the enzyme. Unexpectedly, a DNA sample from a healthy individual is cut, at the set of genomic loci disclosed herein, more extensively then a DNA sample from a cancer patient. Accordingly, the difference in digestion efficiency between a DNA sample in which the restriction loci of the invention are highly methylated and a DNA sample in which these loci have low methylation levels establishes different amplification patterns in subsequent amplification and quantification steps. Surprisingly, the difference in the amplification patterns allows distinguishing between DNA from a lung cancer patient and DNA from a healthy individual with no lung cancer.

The amplification and quantification steps according to the methods and kits of the present invention involve co-amplification of at least one restriction locus and a control locus from the digested DNA. The control locus may be a locus that is not cut by the methylation-sensitive restriction enzyme used in the digestion step. Signal intensities of the amplified loci are then determined, and a ratio is calculated between the signal intensities of each restriction locus and the control locus. It is now disclosed for the first time that distinct signal ratios are produced for DNA from lung cancer patients and for DNA from healthy individuals, thus enabling identification of lung cancer.

The identification of lung cancer is performed by comparing signal ratios calculated for DNA from a tested subject to one or more reference ratios determined for the same restriction and control loci in known sources, i.e., in normal individuals and/or in cancer patients. Based on the comparison, the tested sample is identified as derived from a cancer patient or from a healthy subject. It should be noted that at no point the kits and methods of the invention require determination of methylation level of individual loci per se.

The methods and kits of the present invention enable identification of lung cancer by testing plasma samples, thus advantageously providing non-invasive molecular-based screening and diagnosis of the disease. Another benefit of the claimed methods and kits is that identification may be carried out in a plasma sample despite the low amounts of tumor-derived DNA that plasma samples may contain. Additional benefit conferred by diagnosing lung cancer by the methods and kits disclosed herein is the high sensitivity and specificity of the diagnosis. In addition, the methodology described herein produces an objective result which is not user-dependent.

According to one aspect, the present invention provides a method for identifying lung cancer in a human subject, the method comprising:

(a) subjecting DNA from a sample obtained from the subject to digestion with at least one methylation-sensitive restriction endonuclease, thereby obtaining restriction endonuclease-treated DNA;

(b) co-amplifying from the restriction endonuclease-treated DNA at least one restriction locus and a control locus, wherein the at least one restriction locus is selected from the group consisting of SEQ ID NO: 1, SEQ ID NO: 2, SEQ ID NO: 3, SEQ ID NO: 4, SEQ ID NO: 5 and SEQ ID NO: 6, thereby generating an amplification product for each locus;

(c) determining a signal intensity for each generated amplification product; and (d) comparing a ratio between the signal intensities of the amplification products of each of said at least one restriction locus and the control locus to at least one reference ratio to determine whether lung cancer is present in the human subject.

In some embodiments, the sample is a plasma sample.

In some embodiments, the control locus is a locus devoid of a recognition sequence of the methylation-sensitive restriction endonuclease.

In some embodiments, the at least one reference ratio comprises a healthy reference ratio.

In some embodiments, the at least one reference ratio comprises a lung cancer reference ratio.

In some embodiments, step (a) is performed using a single methylation-sensitive restriction endonuclease. In some embodiments, the methylation-sensitive restriction endonuclease is selected from HinP1I and HhaI.

In some embodiments, step (b) is performed using real-time PCR. In some embodiments, when step (b) is performed using real-time PCR, the method further comprises adding fluorescent probes for assisting in detecting the amplification products of the at least one restriction locus and the control locus. In some embodiments, the ratio between the signal intensities of the amplification products of each of said at least one restriction locus and the control locus is calculated by determining the quantification cycle (Cq) for each locus and calculating $2^{(Cq\ control\ locus - Cq\ restriction\ locus)}$.

In some embodiments, the at least one restriction locus comprises the locus set forth in SEQ ID NO: 4, and optionally at least one additional restriction locus selected from the group of loci set forth in SEQ ID NO: 1, SEQ ID NO: 2, SEQ ID NO: 3, SEQ ID NO: 5 and SEQ ID NO: 6.

In some embodiments, the at least one restriction locus comprises all loci set forth in SEQ ID NO: 1, SEQ ID NO: 2, SEQ ID NO: 3, SEQ ID NO: 5 and SEQ ID NO: 6.

In some embodiments, the method further comprises:

providing first and second control DNA, each comprising human cell line-derived DNA, wherein the first control DNA comprises DNA from a human cell line in which the at least one restriction locus disclosed herein is mostly methylated, and the second control DNA comprises DNA from a human cell line in which one or more of the at least one restriction locus disclosed herein is mostly unmethylated;

digesting the first and second control DNA with the methylation-sensitive restriction endonuclease; and amplifying from the first and second control DNA the at least one restriction locus and the control locus, wherein detection of adequate amplification of the at least one restriction locus and the control locus in the first control DNA is indicative of successful DNA amplification, and wherein low or absence of amplification of one or more of the at least one restriction locus concomitant with normal amplification of the control locus in the second control DNA is indicative of successful DNA digestion.

In some embodiments, the human cell line in which the at least one restriction locus is mostly methylated is HCT-15.

In some embodiments, the human cell line in which one or more restriction locus is mostly unmethylated is A673.

In some embodiments, the human cell line in which the at least one restriction locus is mostly methylated is HCT-15 and the human cell line in which one or more restriction locus is mostly unmethylated is A673.

In some embodiments, the control locus is the locus set forth in SEQ ID NO: 7.

According to another aspect, the present invention provides a method for measuring methylation ratio of DNA from a human subject suspected of having lung cancer, the method comprising: (a) subjecting DNA from a sample obtained from the subject to digestion with at least one methylation-sensitive restriction endonuclease, thereby obtaining restriction endonuclease-treated DNA; (b) co-amplifying from the restriction endonuclease-treated DNA at least one restriction locus and a control locus, wherein the at least one restriction locus is selected from the group consisting of SEQ ID NO: 1, SEQ ID NO: 2, SEQ ID NO: 3, SEQ ID NO: 4, SEQ ID NO: 5 and SEQ ID NO: 6, thereby generating an amplification product for each locus; (c) determining a signal intensity for each generated amplification product; and (d) calculating a ratio between the signal intensities of the amplification products of each of said at least one restriction locus and the control locus, thereby measuring methylation ratio of the DNA from the human subject.

In some embodiments, the sample is a plasma sample.

According to yet another aspect, there is provided herein a method of screening for lung cancer in a human subject, the method comprising:

measuring methylation ratio of DNA from the human subject as described above; and determining that lung cancer is present in the human subject based on the methylation ratio.

According to yet another aspect, there is provided herein a method of screening for lung cancer in a human subject, the method comprising:

identifying whether lung cancer is present in the human subject by carrying out the method of the present invention of identifying lung cancer on DNA from a sample of said subject; and carrying out a definitive diagnosis of lung cancer by biopsy when the subject is identified as having lung cancer.

In some embodiments, the sample is a plasma sample.

According to a further aspect, there is provided herein a kit for identification of lung cancer in a human subject, the kit comprising: at least one methylation-sensitive restriction enzyme for digesting DNA from a sample from a human subject; and a plurality of primer pairs for co-amplification of at least one restriction locus and a control locus following digestion with the at least one methylation-sensitive restriction enzyme, wherein the at least one restriction locus is selected from the group consisting of SEQ ID NO: 1, SEQ ID NO: 2, SEQ ID NO: 3, SEQ ID NO: 4, SEQ ID NO: 5 and SEQ ID NO: 6.

In some embodiments, the sample is a plasma sample.

In some embodiments, the kit further comprises a plurality of polynucleotide probes for detecting amplification products of the at least one restriction locus and the control locus.

In some embodiments, the kit further comprises instructions for carrying out the identification of lung cancer using a computer software stored on a computer-readable medium, the computer software directs a computer processor to perform the following steps: determining signal intensities for the at least one restriction locus and the control locus following their amplification; calculating signal ratios between the signal intensities of each of the at least one restriction locus and the control locus; comparing the calculated signal ratios to at least one reference ratio; and based on the comparison, outputting whether the DNA sample is lung cancer DNA or healthy DNA.

In some embodiments, the kit further comprises a computer readable medium storing a computer software that directs a computer processor to perform the following steps: determining signal intensities for the at least one restriction locus and the control locus following their amplification; calculating signal ratios between the signal intensities of each of the at least one restriction locus and the control locus; comparing the calculated signal ratios to at least one reference ratio; and based on the comparison, outputting whether the DNA sample is lung cancer DNA or healthy DNA.

In some embodiments, the kit comprises a single methylation-sensitive endonuclease. In some embodiments, the methylation-sensitive endonuclease is selected from HinP1I and HhaI.

According to a further aspect, there is provided herein a system for identifying lung cancer in a human subject, the system comprising:

(i) at least one methylation-sensitive restriction endonuclease for digesting DNA from a sample from a human subject;

(ii) a plurality of primer pairs for co-amplification of at least one restriction locus and at least one control locus following digestion with the at least one methylation-sensitive restriction enzyme, wherein the at least one restriction locus is selected from the group consisting of SEQ ID NO: 1, SEQ ID NO: 2, SEQ ID NO: 3, SEQ ID NO: 4, SEQ ID NO: 5 and SEQ ID NO: 6; and (iii) computer software stored on a computer readable medium, the computer software directs a computer processor to perform the following steps: determining signal intensities for the at least one restriction locus and the control locus following their amplification; calculating signal ratios between the signal intensities of each of the at least one restriction locus and the control locus; comparing the calculated signal ratios to at least one reference ratio; and based on the comparison, outputting whether the DNA sample is lung cancer DNA or healthy DNA.

In some embodiments, the sample is a plasma sample.

These and further aspects and features of the present invention will become apparent from the detailed description, examples and claims which follow.

DETAILED DESCRIPTION OF THE INVENTION

Figure 1A:
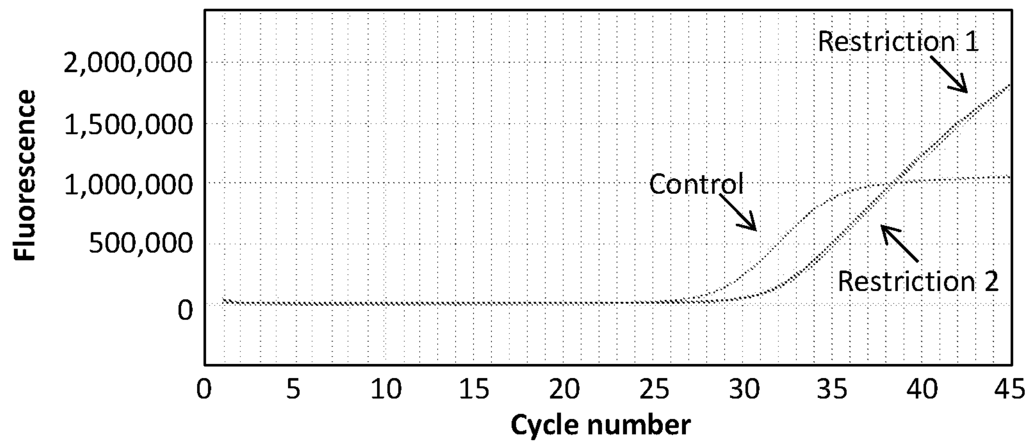
FIG. 1A exhibits exemplary amplification plots of a control locus and two restriction loci in a sample from a healthy subject.

The present invention relates to identification of lung cancer using DNA from plasma samples based on detection of alterations in DNA methylation at defined loci.

The present invention involves calculating signal intensity ratios between selected loci co-amplified from a tested DNA sample following digestion of the DNA with at least one methylation sensitive restriction enzyme, and comparing these ratios to one or more reference ratios obtained from a plurality of DNA samples derived from a known source, healthy or lung cancer. Based on the comparison, the tested sample is identified as derived from a cancer patient or from a healthy subject.

The term "plurality" as used herein refers to 'at least two' or 'two or more'.

The methods of the present invention are particularly beneficial, as they provide highly sensitive and specific means for screening and/or diagnosing lung cancer which are non-invasive and user-independent. Surprisingly, the methods and kits disclosed herein provide accurate diagnosis of lung cancer based on DNA in plasma, despite the fact that plasma samples contain low amounts of tumor-derived DNA.

Furthermore, in contrast to conventional methods utilizing methylation analysis for distinguishing between tumor-derived and normal DNA, which require determining actual methylation levels at specific genomic loci, the methodology described herein does not require to evaluate absolute methylation levels. The methods disclosed herein therefore eliminate the need for standard curves and/or additional laborious steps involved in determination of methylation levels per se, thereby offering a simple and cost effective procedure. An additional advantage over known approaches for analyzing methylation is conferred by the signal ratios obtained by the methods of the invention, which are calculated between loci amplified from the same DNA template in the same reaction mixture (i.e., under the same reaction conditions). This renders the methods insensitive to various "noise" factors, such as changes in template DNA concentration, PCR conditions, and presence of inhibitors. Such noises are inherent for existing methods that are based on quantifying methylation levels of loci by comparing signals from separate amplification reactions.

Methylation in the human genome occurs in the form of 5-methyl cytosine and is confined to cytosine residues that are part of the sequence CG, also denoted as CpG dinucleotides (cytosine residues that are part of other sequences are not methylated). Some CG dinucleotides in the human genome are methylated, and others are not. In addition, methylation is cell and tissue specific, such that a specific CG dinucleotide can be methylated in a certain cell and at the same time unmethylated in a different cell, or methylated in a certain tissue and at the same time unmethylated in different tissues. DNA methylation is an important regulator of gene transcription.

The methylation pattern of cancer DNA differs from that of normal DNA, wherein some loci are hypermethylated while others are hypomethylated. This aberrant methylation pattern can be detected in tumor derived DNA in body fluids such as blood plasma, facilitating the development of non-invasive, 'liquid biopsy' type of assays, for early detection, companion diagnostics, monitoring of response to treatment, detection of relapses, and prognosis. However, body fluids also contain a large amount of DNA from normal cells, and therefore in order for the liquid biopsy assay to be effective, it should be able to detect a small number of tumor derived DNA on a background of a much larger number of normal DNA molecules. The present invention advantageously provides methods for detection of hypermethylated genomic loci associated with lung cancer. The methods are based on enzymatic digestion of DNA with a methylation-sensitive enzyme followed by real time PCR of a hypermethylated target locus and an internal reference locus, and precise quantification of the ratio between the signals obtained from the two loci. The methods disclosed herein are highly sensitive yet specific in identifying plasma samples from subjects with lung cancer.

In some embodiments, there is provided a method identifying lung cancer in a human subject, the method comprising: (a) digesting DNA from a plasma sample obtained from the human subject with at least one methylation-sensitive restriction endonuclease; (b) co-amplifying from the restriction endonuclease-treated DNA at least one restriction locus and a control locus, wherein the at least one restriction locus is selected from the group consisting of SEQ ID NO: 1, SEQ ID NO: 2, SEQ ID NO: 3, SEQ ID NO: 4, SEQ ID NO: 5 and SEQ ID NO: 6, thereby generating an amplification product for each locus; (c) determining a signal intensity for each generated amplification product; (d) calculating a ratio between the signal intensities of the amplification products of the restriction locus and the control locus in said DNA sample; and (e) detecting a high probability score, above a predefined threshold, for said ratio with respect to lung cancer ratio, thereby identifying lung cancer in the human subject.

In some embodiments, there is provided a method for identifying lung cancer in a human subject, the method comprising: (a) digesting DNA from a plasma sample obtained from the subject with at least one methylation-sensitive restriction endonuclease; (b) amplifying at least the restriction locus set forth in SEQ ID NO: 4 and a control locus in the digested DNA sample, wherein the control locus is a locus exhibiting the same digestion and amplification profile in lung cancer DNA and in normal DNA, thereby generating an amplification product for each locus in said DNA sample; (c) determining a signal intensity for each generated amplification product; (d) calculating a ratio between the signal intensities of the amplification products of the restriction locus and the control locus in said DNA sample; and (e) detecting a high probability score, above a predefined threshold, for said ratio with respect to lung cancer ratio, thereby identifying lung cancer in the human subject.

In some embodiments, detecting a high probability score for said ratio with respect to lung cancer ratio comprises detecting a probability score that is above a predefined threshold.

In some embodiments, the method of the present invention comprises calculating signal ratios for a tested DNA sample and comparing the calculated signal ratios to corresponding healthy reference ratios, lung cancer references ratios or both, and identifying the tested DNA sample as lung cancer DNA sample based on the comparison.

In some embodiments, detecting a high probability score with respect to lung cancer ratio comprises comparing a ratio calculated for a tested DNA sample to a corresponding healthy reference ratio, and assigning a probability score reflecting the probability that the calculated ratio is a lung cancer ratio (i.e., representing lung cancer) based on the comparison, wherein a high probability score, above a predefined threshold, is indicative of lung cancer.

In additional embodiments, detecting a high probability score with respect to lung cancer ratio comprises comparing a ratio calculated for a tested DNA sample to a corresponding lung cancer reference ratio, and assigning a probability score reflecting the probability that the calculated ratio is a lung cancer ratio based on the comparison, wherein a high probability score, above a predefined threshold, is indicative of lung cancer.

In yet additional embodiments, detecting a high probability score with respect to lung cancer ratio comprises comparing a ratio calculated for a tested DNA sample to a corresponding healthy reference ratio and a corresponding lung cancer reference ratio, and assigning a probability score reflecting the probability that the calculated ratio is a lung cancer ratio based on the comparison, wherein a high probability score, above a predefined threshold, is indicative of lung cancer.

Thus, in some embodiments, the method of the present invention comprises providing at least one of: healthy reference ratios and lung cancer reference ratios.

In some embodiments, the method comprises comparing the ratio calculated for a tested sample to a reference scale comprising a plurality of ratios determined in lung cancer patients and/or in healthy individuals, wherein said probability score is a score assigned to said calculated ratio based on its relative position within the reference scale. In some embodiments, the higher the value of the ratio, the higher the score assigned thereto.

In some embodiments, the method comprises amplifying the restriction locus set forth in SEQ ID NO: 4 and at least one additional restriction locus, thereby generating an amplification product for the at least one additional restriction locus; and repeating steps (c)-(d) for each additional restriction locus. In some embodiments, a plurality of probability scores is obtained for a plurality of ratios with respect to corresponding lung cancer reference ratios, wherein each ratio is between a distinct restriction locus and the control locus. In some embodiments, a combined probability score is calculated based on the plurality of probability scores.

In some embodiments, the combined score may be an average score. In other embodiments, the combined score may be a weighted average of the plurality of probability scores. In some embodiments, the combined score may be a sum of all probability scores. In general, the combined score may include any mathematical or statistic value which represents all probability scores.

In some embodiments, detecting a high combined probability score identifies lung cancer in the human subject. In some embodiments, detecting a high combined probability score is detecting a combined probability score that is above a pre-defined threshold.

The terms "DNA from", "DNA derived from", "DNA within" and the like are interchangeable and refer to DNA obtained from a sample, e.g., a plasma sample, DNA isolated from a sample or a sample as is namely, a sample containing DNA therewith.

According to the present invention, the DNA is obtained from accessible samples, without the need for biopsy. In some embodiments, the DNA is obtained from plasma or serum. In other embodiments, the DNA is obtained by bronchial lavage.

The term "lung cancer" refers to malignant tumors arising from cells in the lungs. Lung cancer is used herein to include non-small cell lung cancer (NSCLC) (subtypes squamous cell carcinoma, adenocarcinoma and large cell carcinoma) and small cell lung cancer. In addition to type, lung cancer is also typically characterized by stage based on, e.g. biopsy staining and/or imaging, including stage I, stage II, stage III and stage IV.

In some embodiments, the lung cancer is non-small cell lung cancer. In some particular embodiments, the non-small cell lung cancer is squamous cell carcinoma. In additional particular embodiments, the non-small cell lung cancer is adenocarcinoma. In yet additional particular embodiments, the non-small cell lung cancer is large cell carcinoma. In other embodiments, the lung cancer is small cell lung cancer.

The terms "identification of lung cancer", "identifying lung cancer in a subject" and "identifies the subject as having lung cancer" as used herein are interchangeable and encompass any one or more of screening for lung cancer, detecting the presence of lung cancer, detecting recurrence of lung cancer, detecting susceptibility to lung cancer, detecting response to treatment of lung cancer, determining efficacy of treatment to lung cancer, determining stage (severity) of lung cancer, determining prognosis of lung cancer and early diagnosis of lung cancer in a subject. Each possibility represents a separate embodiment of the present invention.

The term "subject" as used herein is interchangeable with "individual" and refers to a human subject. The subject may be suspected of having lung cancer. In some embodiments, the subject may be at risk of developing lung cancer, for example, based on previous history of the disease, genetic predisposition, and/or family history, a subject who has been exposed to any one or more of carcinogens, occupational hazard, environmental hazard and/or a subject who exhibits suspicious clinical signs of cancer. In some embodiments, the subject may show at least one symptom or characteristic of lung cancer, including for example, respiratory symptoms such as coughing, coughing up blood, wheezing, or shortness of breath, systemic symptoms such as weight loss, weakness and fever, and symptoms due to the cancer mass pressing on adjacent structures such as chest pain, bone pain or difficulty swallowing. In other embodiments, the subject may be asymptomatic.

Plasma Sample Collection and Processing

The term "plasma" refers to the liquid remaining after a whole blood sample is subjected to a separation process to remove the blood cells. The plasma samples may be samples separated from whole blood using any method of separation, including for example by centrifugation and/or filtration. The plasma samples may be collected using conventional collection containers or tubes.

In some embodiments, genomic DNA may be extracted from the plasma samples according to methods known in the art. Exemplary procedures are described, e.g., in Sambrook et al, Molecular Cloning: A Laboratory Manual, Fourth Ed., Cold Spring Harbor Laboratory Press, Cold Spring Harbor, NY, 2012.

DNA Digestion

According to the methods of the present invention, DNA from the plasma sample is subjected to digestion with at least one methylation-sensitive restriction endonuclease, for example, with one, two, three methylation-sensitive restriction endonucleases. Each possibility represents a separate embodiment of the present invention.

In some embodiments, the entire DNA that is extracted from the plasma sample is used in the digestion step. In some embodiments, the DNA is not quantified prior to being subjected to digestion. In other embodiments, the DNA may be quantified prior to digestion thereof.

A "restriction endonuclease", used herein interchangeably with a "restriction enzyme", refers to an enzyme that cuts DNA at or near specific recognition nucleotide sequences, known as restriction sites.

A "methylation-sensitive" restriction endonuclease is a restriction endonuclease that cleaves its recognition sequence only if it is unmethylated (while methylated sites remain intact). Thus, the extent of digestion of a DNA sample by a methylation-sensitive restriction endonuclease depends on the methylation level, where a higher methylation level protects from cleavage and accordingly results in less digestion.

In some embodiments, the at least one methylation-sensitive restriction endonuclease may be selected from the group consisting of: AatII, Acc65I, AccI, Aci1, ACII, Afe1, Age1, Apa1, ApaLI, AscI, AsiSI, Ava1, AvaII, BaeI, BanI, BbeI, BceAI, BcgI, BfuCI, Bg1I, BmgBI, BsaAI, BsaBI, BsaHI, BsaI, BseYI, BsiEI, BsiWI, Bs1I, BsmAI, BsmBI, BsmFI, BspDI, BsrBI, BsrFI, BssHII, BssKI, BstAPI, BstBI, BstUI, BstZ17I, Cac8I, C1aI, DpnI, DrdI, EaeI, EagI, Eag1-HF, EciI, EcoRI, EcoRI-HF, FauI, Fnu4HI, FseI, FspI, HaeII, HgaI, HhaI, HincII, HincII, Hinf1, HinP1I, HpaI, HpaII, Hpy166ii, Hpy188iii, Hpy99I, HpyCH4IV, KasI, M1uI, MmeI, MspA1I, MwoI, NaeI, NacI, NgoNIV, Nhe-HFI, NheI, N1aIV, NotI, NotI-HF, NruI, Nt.BbvCI, Nt.BsmAI, Nt.CviPII, PaeR7I, P1eI, PmeI, Pm1I, PshAI, PspOMI, PvuI, RsaI, RsrII, SacII, Sa11, Sa1I-HF, Sau3AI, Sau96I, ScrFI, SfiI, SfoI, SgrAI, SmaI, SnaBI, TfiI, TscI, TseI, TspMI, and ZraI. Each possibility represents a separate embodiment of the present invention.

In some embodiments, DNA from the plasma sample may be subjected to digestion with one methylation-sensitive restriction endonuclease. In some particular embodiments, the methylation-sensitive restriction endonuclease may be HinP1I.

In some embodiments, DNA digestion may be carried out to complete digestion. In some embodiments, the methylation-sensitive restriction endonuclease may be HinP1I, and complete digestion may be achieved following one to two hours incubation with the enzyme at 37° C.

In some embodiments, the plasma sample may be subjected to digestion with one methylation-sensitive restriction endonuclease. In some particular embodiments, the methylation-sensitive restriction endonuclease may be HhaI.

In some embodiments, DNA digestion may be carried out to complete digestion. In some embodiments, the methylation-sensitive restriction endonuclease may be HhaI, and complete digestion may be achieved following one to two hours incubation with the enzyme at 37° C.

Amplification of Genomic Loci

The terms "genomic locus" or "locus" as used herein are interchangeable and refer to a DNA sequence at a specific position on a chromosome. The specific position may be identified by the molecular location, namely, by the numbers of the starting and ending base pairs on the chromosome. As used herein, these terms also encompass the DNA sequence at the specific position along with 5' and/or 3' flanking sequences, of up to about 50 bases immediately upstream and/or downstream of said DNA sequence.

In some embodiments, the 5' flanking sequences may include between 1-50 bases. In additional embodiments, the 5' flanking sequences are of between 10-40 bases. For example, the 5' flanking sequences may include up to 10 bases, up to 15 bases, up to 20 bases, up to 25 bases, up to 30 bases, up to 35 bases, up to 40 bases, up to 45 bases, or up to 50 bases immediately upstream of the locus. Each possibility represents a separate embodiment of the present invention.

In some embodiments, the 3' flanking sequences may include between 1-50 bases. In additional embodiments, the 3' flanking sequences are of between 10-40 bases. For example, the 3' flanking sequences may include up to 10 bases, up to 15 bases, up to 20 bases, up to 25 bases, up to 30 bases, up to 35 bases, up to 40 bases, up to 45 bases, or up to 50 bases immediately downstream of the locus. Each possibility represents a separate embodiment of the present invention.

A variant of a DNA sequence at a given genomic position is called an allele. Alleles of a locus are located at identical sites on homologous chromosomes. Loci include gene sequences as well as other genetic elements (e.g., intergenic sequences).

A “restriction locus” is used herein to describe a locus that contains the recognition sequence of a methylation-sensitive restriction enzyme that is used in the method.

A “control locus” and “internal reference locus” are interchangeable and used herein to describe a locus the digestion of which, with the restriction enzyme applied in the digestion step, is independent of the presence or absence of cancer. In some embodiments, the control locus is a locus that exhibits the same digestion and amplification profile in lung cancer DNA and in normal DNA. In some embodiments, the control locus is a locus devoid of the recognition sequence of the restriction enzyme applied in the digestion step. Advantageously, the control locus is an internal locus, i.e. a locus within the analyzed DNA sample, thus eliminating the need for external/additional control sample(s).

In some embodiments, the restriction locus or restriction loci include any one or more of the loci set forth in SEQ ID NOs: 1-6, as follows:

SEQ ID NO: 1, corresponds to a restriction locus at position 43030476 on chromosome 5 (intergenic region);

SEQ ID NO: 2, corresponds to a restriction locus at position 176712760 on chromosome 2 (intergenic region);

SEQ ID NO: 3, corresponds to a restriction locus at position 44151837 on chromosome 17, (intergenic region);

SEQ ID NO: 4, corresponds to a restriction locus at position 168907269 on chromosome 1, (PRRX1 gene);

SEQ ID NO: 5, corresponds to a restriction locus at position 158629293 on chromosome 7, (VIPR2 gene);

SEQ ID NO: 6, corresponds to a restriction locus at position 154860262 on chromosome 7, (intergenic region);

Unexpectedly, the restriction loci set forth in SEQ ID NOs: 1-6 were identified by the inventors of the present invention to be differentially methylated between DNA from plasma of lung cancer patients and DNA from plasma of healthy subjects. More particularly, these loci have increased methylation in lung cancer DNA (DNA derived from a lung tumor) compared to normal non-cancerous DNA.

Each of these loci contains CG dinucleotides that are more methylated in lung cancer DNA compared to normal non-cancerous DNA. Advantageously, the differentially methylated CG dinucleotides are located within recognition sites of methylation-sensitive restriction enzymes.

In some embodiments, each of these loci may contain at least one restriction site of a methylation-sensitive restriction enzyme in which the CG dinucleotide is more methylated in DNA from plasma of lung cancer patients than in DNA from plasma of healthy subjects, meaning that in the plasma of lung cancer patients a greater number of DNA molecules are methylated at this position compared to plasma of healthy subjects. In some embodiments, each of these loci may contain at least one HinP1I restriction site (GCGC). Such methylation-sensitive restriction enzyme cleaves its recognition sequence only if it is unmethylated. Thus, a DNA sample containing a higher percentage of DNA molecules in which the CG dinucleotide in the restriction site is methylated would be digested to a lesser extent compared to a DNA sample containing a higher percentage of DNA molecules in which the CG dinucleotide is unmethylated. Based on the methods disclosed herein, DNA digestion by methylation-sensitive restriction enzymes is less extensive for DNA from plasma samples of lung cancer patients compared to DNA from normal (healthy) individuals. It was surprisingly found that the difference in digestion efficiency establishes different amplification patterns in subsequent amplification and quantification steps, which enables distinguishing between DNA from a lung cancer patient and DNA from a healthy subject.

In some embodiments, each of the loci set forth in SEQ ID NOs: 1-6 may contain additional CG dinucleotides whose methylation status is of no relevance or influence on the assay—only methylation at the recognition sequence of the restriction enzyme (e.g. HinP1I) is relevant.

In some embodiments, the control locus is as set forth in SEQ ID NO: 7, which corresponds to position 121380854-121380913 on chromosome 7 (intergenic region).

In some embodiments, the control locus, also termed an internal reference locus, does not contain a recognition sequence of the restriction enzyme. In some embodiments, the sequence of the control locus remains intact regardless of its methylation status when a DNA sample is digested with a methylation-sensitive restriction enzyme.

In some embodiments, the sequence of the control locus exhibits the same digestion and amplification profile in lung cancer DNA and in normal DNA.

In some embodiments, the control locus comprises the locus set forth in SEQ ID NO: 7. The amplification pattern of the control locus following digestion with the methylation sensitive restriction enzyme is not affected by methylation.

The advantage in using the restriction loci set forth in SEQ ID NOs: 1-6 for differentiating between plasma samples of lung cancer patients and those of healthy individuals is exemplified herein below using the methylation sensitive restriction enzymes HinP1I. Amplification of restriction loci comprising each of SEQ ID NOs: 1-6 and of a control locus comprising SEQ ID NO: 7 following digestion with HinP1I was carried out in plasma DNA from cancer patients and healthy individuals. Calculation of signal ratios between the amplification products of each restriction locus and the control locus showed significantly higher signal ratios (at least one order of magnitude higher) in the cancer group compared to the control group.

In some embodiments, the method comprises amplifying at least one restriction locus and at least one control locus following digestion of the DNA sample.

As used herein, “at least one (restriction/control) locus”, may encompass a single locus or a plurality of separate loci, such that, a phrase such as “at least one restriction locus comprising the locus set forth in SEQ ID NO: 1 and the locus set forth in SEQ ID NO: 2” indicates that at least these two separate genomic loci are amplified.

In some embodiments, the method comprises amplifying a restriction locus comprising the sequence set forth in SEQ ID NO: 1 and a control locus, and optionally at least one additional restriction locus.

In some embodiments, the method comprises amplifying a restriction locus comprising the sequence set forth in SEQ ID NO: 2 and a control locus, and optionally at least one additional restriction locus.

In some embodiments, the method comprises amplifying a restriction locus comprising the sequence set forth in SEQ ID NO: 3 and a control locus, and optionally at least one additional restriction locus.

In some embodiments, the method comprises amplifying a restriction locus comprising the sequence set forth in SEQ ID NO: 4 and a control locus, and optionally at least one additional restriction locus.

In some embodiments, the method comprises amplifying a restriction locus comprising the sequence set forth in SEQ ID NO: 5 and a control locus, and optionally at least one additional restriction locus.

In some embodiments, the method comprises amplifying a restriction locus comprising the sequence set forth in SEQ ID NO: 6 and a control locus, and optionally at least one additional restriction locus.

In some embodiments, the method comprises amplifying a restriction locus comprising the sequence set forth in SEQ ID NO: 4 and a control locus comprising the sequence set forth in SEQ ID NO: 7.

In some embodiments, the method comprises amplifying a plurality of restriction loci (i.e., at least two restriction loci) and a control locus.

In some embodiments, the plurality of restriction loci comprises a restriction locus comprising the sequence set forth in SEQ ID NO: 1 and at least one additional restriction locus comprising a sequence selected from the group consisting of SEQ ID NO: 2, SEQ ID NO: 3, SEQ ID NO: 4, SEQ ID NO: 5 and SEQ ID NO: 6. Each possibility represents a separate embodiment of the present invention.

In some embodiments, the plurality of restriction loci comprises a restriction locus comprising the sequence set forth in SEQ ID NO: 2 and at least one additional restriction locus comprising a sequence selected from the group consisting of SEQ ID NO: 1, SEQ ID NO: 3, SEQ ID NO: 4, SEQ ID NO: 5 and SEQ ID NO: 6. Each possibility represents a separate embodiment of the present invention.

In some embodiments, the plurality of restriction loci comprises a restriction locus comprising the sequence set forth in SEQ ID NO: 3 and at least one additional restriction locus comprising a sequence selected from the group consisting of SEQ ID NO: 1, SEQ ID NO: 2, SEQ ID NO: 4, SEQ ID NO: 5 and SEQ ID NO: 6. Each possibility represents a separate embodiment of the present invention.

In some embodiments, the plurality of restriction loci comprises a restriction locus comprising the sequence set forth in SEQ ID NO: 4 and at least one additional restriction locus comprising a sequence selected from the group consisting of SEQ ID NO: 1, SEQ ID NO: 2, SEQ ID NO: 3, SEQ ID NO: 5 and SEQ ID NO: 6. Each possibility represents a separate embodiment of the present invention.

In some embodiments, the plurality of restriction loci comprises a restriction locus comprising the sequence set forth in SEQ ID NO: 5 and at least one additional restriction locus comprising a sequence selected from the group consisting of SEQ ID NO: 1, SEQ ID NO: 2, SEQ ID NO: 3, SEQ ID NO: 4, and SEQ ID NO: 6. Each possibility represents a separate embodiment of the present invention.

In some embodiments, the plurality of restriction loci comprises a restriction locus comprising the sequence set forth in SEQ ID NO: 6 and at least one additional restriction locus comprising a sequence selected from the group consisting of SEQ ID NO: 1, SEQ ID NO: 2, SEQ ID NO: 3, SEQ ID NO: 4 and SEQ ID NO: 5. Each possibility represents a separate embodiment of the present invention.

In some embodiments, the plurality of restriction loci comprises a locus comprising the sequence set forth as SEQ ID NO: 4 and further comprises one, two, three, four, five, additional restriction loci comprising sequences selected from the group consisting of SEQ ID NOs: 1, 2, 3, 5 and 6. Each possibility represents a separate embodiment of the present invention.

In some embodiments, the plurality of restriction loci comprises loci comprising the sequences set forth as SEQ ID NOs: 1-6. In some embodiments, the plurality of restriction loci is consisting of the restriction loci set forth in SEQ ID NOs: 1-6. In some embodiments, the method comprises amplifying a plurality of restriction loci as set forth SEQ ID NOs: 1-6.

As used herein, "amplification" refers to an increase in the number of copies of one or more particular nucleic acid target of interest. Amplification is typically performed by polymerase chain reaction (PCR) in the presence of a PCR reaction mixture which may include a suitable buffer supplemented with the DNA template, polymerase (usually Taq Polymerase), dNTPs, primers and probes (as appropriate), as known in the art.

The term "polynucleotide" as used herein include polymeric forms of nucleotides of any length, either deoxyribonucleotides or ribonucleotides, or analogs thereof. The term "oligonucleotide" is also used herein to include a polymeric form of nucleotides, typically of up to 100 bases in length.

An "amplification product" collectively refers to nucleic acid molecules of a particular target sequence that are generated and accumulated in an amplification reaction. The term generally refers to nucleic acid molecules generated by PCR using a given set of amplification primers.

As used herein, a "primer" defines an oligonucleotide which is capable of annealing to (hybridizing with) a target sequence, thereby creating a double stranded region which can serve as an initiation point for DNA synthesis under suitable conditions. The terminology "primer pair" refers herein to a pair of oligonucleotides which are selected to be used together in amplifying a selected nucleic acid sequence by one of a number of types of amplification processes, preferably PCR. As commonly known in the art, the primers may be designed to bind to a complementary sequence under selected conditions.

The primers may be of any suitable length, depending on the particular assay format and the particular needs. In some embodiments, the primers may include at least 15 nucleotides in length, preferably between 19-25 nucleotides in length. The primers may be adapted to be especially suited to a chosen nucleic acid amplification system. As commonly known in the art, the oligonucleotide primers may be designed by taking into consideration the melting point of hybridization thereof with their targeted sequence (Sambrook et al, ibid).

In some embodiments, the restriction and control loci may be amplified from the same DNA sample (the digested sample) using pairs of reverse and forward primers designed as known in the art to specifically amplify each locus. In some embodiments, the primers may be designed to amplify a locus along with 5' and 3' flanking sequences thereof.

In some embodiments, the 5' flanking sequences may include between 1-60 bases. In additional embodiments, the 5' flanking sequences are of between 10-50 bases. For example, the 5' flanking sequences may include 10 bases, 15 bases, 20 bases, 25 bases, 30 bases, 35 bases, 40 bases, 45 bases, or 50 bases immediately upstream of the locus. Each possibility represents a separate embodiment of the present invention.

In some embodiments, the 3' flanking sequences may include between 1-60 bases. In additional embodiments, the 3' flanking sequences are of between 10-50 bases. For example, the 3' flanking sequences may include 10 bases, 15 bases, 20 bases, 25 bases, 30 bases, 35 bases, 40 bases, 45 bases, or 50 bases immediately downstream of the locus. Each possibility represents a separate embodiment of the present invention.

In some embodiments, the primers may be designed to generate amplification products of between 60-150 bps in length. In some particular embodiments, the primers may be designed to generate amplification products of between 70-140 bps in length.

In some embodiments, the method involves simultaneous amplification of more than one target sequence (at least one restriction locus and one control locus) in the same reaction mixture, a process known as multiplex amplification or co-amplification. This process requires simultaneous use of multiple primer pairs. As known in the art, the primers may be designed such that they can work at the same annealing temperature during amplification. In some embodiments, primers with similar melting temperature (Tm) are used in the method disclosed herein. A Tm variation of between about 3°-5° C. is considered acceptable for primers used in a pool.

In some embodiments, all restriction and control loci may be amplified in a single reaction mixture. In other embodiments, for example due to technical limitation of a particular machine, the digested DNA sample may be divided into several aliquots, each of which is supplemented with primer pairs for amplification of one or more restriction loci and the control locus. Thus, even if a DNA sample is divided into several aliquots, the control locus is amplified in each aliquot, and calculation of signal ratios is performed for the control locus and a restriction locus that are amplified together, i.e., from the same aliquot.

In some embodiments, the method may use one or more control DNA derived from human cell lines in the digestion and amplification step(s).

The control DNA may be used for evaluating the digestion and amplification processes, for example, monitoring the efficacy and quality of the digestion and amplification steps. In some embodiments, the control DNA and the tested DNA sample are digested by the at least one methylation-sensitive restriction enzyme. In some embodiments, the control DNA and the tested DNA sample are subjected to PCR amplification of at least one restriction locus and a control locus.

In some embodiments, a first control DNA comprises DNA from a human cell line in which the at least one restriction locus is mostly methylated. In some particular embodiments, the first control DNA comprises DNA from HCT-15 cell line.

In some embodiments, a second control DNA comprises DNA from a human cell line in which restriction loci disclosed herein are mostly unmethylated. In some particular embodiments, the second control DNA comprises DNA from A673 cell line.

As used herein, “mostly” indicates that the restriction locus is at least 75% and preferably at least 95% methylated/unmethylated.

In the first control DNA, the restriction loci disclosed herein remain mostly intact upon digestion with a methylation-sensitive restriction endonuclease. In a subsequent amplification step, the restriction loci disclosed herein are well amplified. A control locus as disclosed herein is also well amplified in the first control DNA.

Thus, detecting adequate amplification of the restriction loci and the control locus in the first control DNA is indicative that the amplification step in the method of the present invention is successful.

As used herein, “adequate amplification” refers to a fluorescence level above 100,000 units.

In the second control DNA, the restriction loci which are mostly unmethylated are cut extensively upon digestion with a methylation-sensitive restriction endonuclease. In a subsequent amplification step, these restriction loci show low or absence of amplification. A control locus as disclosed herein is well amplified in the second control DNA.

Thus, detecting low or absence of amplification of one or more of the restriction loci concomitant with adequate amplification (as defined above) of the control locus in the second control DNA is indicative that the digestion step in the method of the present invention is successful.

As used herein, “low or absence of amplification” refers to a ΔCq of at least 9 cycles between the Cq of the restriction locos and the Cq of the control locus.

In some embodiments, amplification of the genomic loci may be carried out using real-time PCR (RT-PCR), also known as quantitative PCR (qPCR), in which simultaneous amplification and detection of the amplification products are performed.

In some embodiments, detection of the amplification products in RT-PCR may be achieved using polynucleotide probes, typically fluorescently-labeled polynucleotide probes.

As used herein, “polynucleotide probes” or “oligonucleotide probes” are interchangeable and refer to labeled polynucleotides which are complementary to specific sub-sequences within the nucleic acid sequences of loci of interest, for example, within the sequence of a restriction locus or a control locus. In some embodiments, detection is achieved by using TaqMan assays based on combined reporter and quencher molecules (Roche Molecular Systems Inc.). In such assays, the polynucleotide probes have a fluorescent moiety (fluorophore) attached to their 5' end and a quencher attached to the 3' end. During PCR amplification, the polynucleotide probes selectively hybridize to their target sequences on the template, and as the polymerase replicates the template it also cleaves the polynucleotide probes due to the polymerase's 5'-nuclease activity. When the polynucleotide probes are intact, the close proximity between the quencher and the fluorescent moiety normally results in a low level of background fluorescence. When the polynucleotide probes are cleaved, the quencher is decoupled from the fluorescent moiety, resulting in an increase of intensity of fluorescence. The fluorescent signal correlates with the amount of amplification products, i.e., the signal increases as the amplification products accumulate.

As used herein, “selectively hybridize to” (as well as “selective hybridization,” “specifically hybridize to,” and “specific hybridization”) refers to the binding, duplexing, or hybridizing of a nucleic acid molecule (such as a primer or a probe) preferentially to a particular complementary nucleotide sequence under stringent conditions. The term "stringent conditions" refers to conditions under which a nucleic acid molecule will hybridize preferentially to its target sequence and to a lesser extent to, or not at all to, other non-target sequences. A "stringent hybridization" in the context of nucleic acid hybridization is sequence-dependent, and differs under different conditions, as known in the art.

Polynucleotide probes may vary in length. In some embodiments, the polynucleotide probes may include between 15-30 bases. In additional embodiments, the polynucleotide probes may include between 25-30 bases. In some embodiments, the polynucleotide probes may include between 20-30 bases, for example, 20 bases, 21 bases, 22 bases, 23 bases, 24 bases, 25 bases, 26 bases, 27 bases, 28 bases, 29 bases, 30 bases. Each possibility represents a separate embodiment of the present invention.

Polynucleotide probes may be designed to bind to either strand of the template. Additional considerations include the Tm of the polynucleotide probes, which should preferably be compatible to that of the primers. Computer software may be used for designing the primers and probes.

As noted above, the methods disclosed herein may involve simultaneous amplification of more than one target sequence (at least one restriction locus and one control locus) in the same reaction mixture. In order to distinguish between multiple target sequences that are amplified in parallel, polynucleotide probes labeled with distinct fluorescent colors may be used.

In some embodiments, the polynucleotide probes form fluorophore/quencher pairs as known in the art and include, for example, FAM-TAMRA, FAM-BHQ1, Yakima Yellow-BHQ1, ATTO550-BHQ2 and ROX-BHQ2.

In some embodiments, the dye combinations may be compatible to the RT-PCR thermocycler of choice.

In some embodiments, fluorescence may be monitored during each PCR cycle, providing an amplification plot showing the change of fluorescent signals from the probes as a function of cycle number.

In the context of real-time PCR, the following terminology is used:

"Quantification cycle" ("Cq") refers to the cycle number in which fluorescence increases above a threshold, set automatically by software or manually by the user. In some embodiments, the threshold may be constant for all loci and may be set in advance, prior to carrying out the amplification and detection. In other embodiments, the threshold may be defined separately for each locus after the run, based on the maximum fluorescence level detected for this locus during the amplification cycles.

"Threshold" refers to a value of fluorescence used for Cq determination. In some embodiments, the threshold value may be a value above baseline fluorescence, and/or above background noise, and within the exponential growth phase of the amplification plot.

"Baseline" refers to the initial cycles of PCR where there is little to no change in fluorescence.

Computer software may be used to analyze amplification plots and determine baseline, threshold and Cq.

Following digestion with the at least one methylation-sensitive restriction enzyme, loci in which the CG dinucleotide in the enzyme's recognition site is methylated are amplified with high efficiency, because the DNA molecules are protected from digestion. The result is relatively low Cq values because detectable amplification products are shown following a relatively small (low) number of amplification cycles. Conversely, loci in which the CG dinucleotide in the enzyme's recognition site is unmethylated are cut more extensively during the digestion step, and thus result in higher Cq values in the amplification and quantification step (i.e., show detectable amplification products following a relatively high number of amplification cycles).

In alternative embodiments, amplification and detection of amplification products may be carried out by conventional PCR using fluorescently-labeled primers followed by capillary electrophoresis of amplification products. In some embodiments, following amplification the amplification products are separated by capillary electrophoresis and fluorescent signals are quantified. In some embodiments, an electropherogram plotting the change in fluorescent signals as a function of size (bp) or time from injection may be generated, wherein each peak in the electropherogram corresponds to the amplification product of a single locus. The peak's height (provided for example using "relative fluorescent units", rFU) may represent the intensity of the signal from the amplified locus. Computer software may be used to detect peaks and calculate the fluorescence intensities (peak height) of a set of loci whose amplification products were run on the capillary electrophoresis machine, and subsequently the ratios between the signal intensities.

For DNA samples digested with a methylation-sensitive restriction enzyme, e.g., HinP1I, loci in which the CG dinucleotide in the enzyme's recognition site is methylated produce a relatively strong signal (higher peak) in the electropherogram. Conversely, loci in which the CG dinucleotide in the enzyme's recognition site is unmethylated produce a relatively weak signal (lower peak) in the electropherogram.

In some embodiments, the fluorescent labels of the primers include any one of fluorescein, FAM, lissamine, phycoerythrin, rhodamine, Cy2, Cy3, Cy3.5, Cy5, Cy5.5, Cy7, FluorX, JOE, HEX, NED, VIC and ROX.

Signal Ratio

The term "ratio" or "signal ratio" as used herein refers to the ratio between the intensities of signals obtained from co-amplification of a pair of genomic loci in a single DNA sample (in the same reaction mixture), particularly co-amplification of a restriction locus and a control locus.

As used herein, a "SEQ ID NO: X ratio" refers to the ratio between the signal intensity of the locus set forth in SEQ ID NO: X and the signal intensity of a control locus, following co-amplification of this pair of loci in a DNA sample digested with a restriction enzyme as detailed herein.

The term "signal intensity" as used herein refers to a measure reflecting the amount of locus-specific amplification products corresponding to the initial amount of intact copies of the locus. However, the signal intensity may not indicate actual amounts of amplification products/intact loci, and may not involve calculation of any absolute amounts of amplification products/intact loci. Thus, for calculating ratios of amplicon signals, no standard curve or reference DNA may be needed since it is unnecessary to calculate actual DNA concentrations or DNA methylation level per se.

In some exemplary embodiments, amplification and detection of amplification products are carried out by RT-PCR where the signal intensity of a specific locus may be represented by the Cq calculated for this locus. The signal ratio in this case may be represented by the following calculation: $2^{(Cq\ of\ control\ locus - Cq\ of\ restriction\ locus)}$.

In additional exemplary embodiments, detection of amplification products is carried out by capillary electrophoresis wherein the signal intensity of a specific locus is the number of relative fluorescence units (rfus) of its corresponding peak. The signal ratio may be calculated by dividing the heights of peaks of each restriction locus by the height of the peak of a control locus.

In some embodiments, calculating a ratio between signal intensities of the amplification products of a restriction locus and a control locus in a DNA sample comprises: (i) determining the signal intensity of the amplification product of the restriction locus; (ii) determining the signal intensity of the amplification product of the control locus; and (iii) calculating a ratio between the two signal intensities.

In some embodiments, calculating a ratio between signal intensities of the amplification products of a restriction locus and a control locus in the DNA sample comprises determining the Cq for each locus, and calculating the difference between the Cq of the control locus and the Cq of the restriction locus. In some embodiments, the calculating further comprises applying the following formula: 2^(Cq of control locus−Cq of restriction locus).

In some embodiments, calculating a signal ratio may be calculating a plurality of signal ratios, between each restriction locus and a control locus.

In some embodiments, calculating a signal ratio may be calculating a signal ratio between the restriction locus set forth in SEQ ID NO: 1 and a control locus. In some embodiments, calculating a signal ratio may be calculating a signal ratio between the restriction locus set forth in SEQ ID NO: 2 and a control locus. In some embodiments, calculating a signal ratio may be calculating a signal ratio between the restriction locus set forth in SEQ ID NO: 3 and a control locus. In some embodiments, calculating a signal ratio may be calculating a signal ratio between the restriction locus set forth in SEQ ID NO: 4 and a control locus. In some embodiments, calculating a signal ratio may be calculating a signal ratio between the restriction locus set forth in SEQ ID NO: 5 and a control locus. In some embodiments, calculating a signal ratio may be calculating a signal ratio between the restriction locus set forth in SEQ ID NO: 6 and a control locus.

In some embodiments, a plurality of loci among the loci set forth in SEQ ID NOs: 1-6 are amplified wherein the method comprises calculating ratios between each of the loci set forth SEQ ID NOs: 1-6 and a control locus, e.g., between the locus set forth in SEQ ID NO: 1 and the control locus, between the locus set forth in SEQ ID NO: 2 and the control locus, and so forth.

In some embodiments, computer software may be used for calculating a ratio between signal intensities of amplification products.

Reference Ratio

The terms "reference ratio" or "reference signal ratio" are used interchangeably and refer to a signal intensity ratio determined in DNA from a known source. A reference ratio for a given pair of restriction and control loci may be represented in a number of ways. In some embodiments, the reference ratio for a given pair of loci may be a single ratio. In some embodiments, the reference ratio for a given pair of loci may be a statistic value, such as, the mean value of a large set of reference ratios, obtained from a large set of DNA samples from a known source, e.g., mean value determined in a large group of cancer patients or a mean value determined in a large group of healthy individuals.

In other embodiments, the reference ratio for a given pair of loci may be a plurality of ratios, such as a distribution of ratios determined for this pair of loci in a large set of DNA samples from a known source. In some embodiments, the reference ratio may be a reference scale.

In some embodiments, a reference scale for a given pair of loci may include signal ratios measured for this pair of loci in a plurality of DNA samples from the same reference source. For example, a reference scale of reference lung cancer patients or a reference scale of reference healthy individuals. In other embodiments, a reference scale for a given pair of loci may include signal ratios from both healthy and diseased individuals, i.e. a single scale combining reference ratios from both sources. Generally, when a single scale is used, the values are distributed such that the values from the healthy individuals are at one end of the scale, e.g. below a cutoff, while the values from the cancer patients are at the other end of the scale, e.g., above the cutoff. In some embodiments, a signal ratio calculated for a tested DNA sample from an unknown source may be compared against a reference scale of healthy and/or cancer reference ratios, and the probability score may be a score assigned to the calculated signal ratio based on its relative position within the scale. In some embodiments, the higher the calculated signal ratio the higher the score assigned thereto, and accordingly the probability with respect to lung cancer is high.

The terms "lung cancer reference ratio" or "reference ratio in lung cancer DNA" interchangeably refer to the signal intensity ratio measured between a given restriction locus and a given control locus in DNA from plasma samples of lung cancer patients. The lung cancer reference ratio represents the signal intensity ratio in lung cancer DNA, namely, DNA from plasma samples of lung cancer patients. The lung cancer reference ratio may be a single ratio, a statistic value or a plurality of ratio (e.g., distribution), as detailed above.

The terms "healthy reference ratio", "normal reference ratio" or reference ratio in healthy DNA" interchangeably refer to the signal intensity ratio measured between a given restriction locus and a given control locus in plasma samples from normal individuals. A "healthy" or "normal" individual is defined herein as an individual without detectable lung diseases or symptoms, and/or lung associated diseases including lung cancer, as determined by conventional diagnostic methods. The healthy reference ratio represents the signal intensity ratio in normal DNA, namely, DNA from plasma samples of healthy individuals. The healthy reference ratio may be a single ratio, a statistic value or a plurality of ratios (e.g., distribution), as detailed above.

In some embodiments, the method disclosed herein comprises pre-determination of reference ratios from lung cancer DNA. In some embodiments, the method of the present invention comprises pre-determination of reference ratios from normal DNA.

As noted above, a signal ratio may be determined by various methods, including for example measuring peaks following capillary electrophoresis or calculating Cq following RT-PCR. It is to be understood that the reference ratios and ratios measured for a tested sample of an unknown source in order to determine lung cancer are obtained using the method disclosed herein.

Determining Lung Cancer

In some embodiments, the method disclosed herein is based on evaluating the signal ratios calculated for DNA from a plasma sample of an unknown source compared to reference ratios in order to identify lung cancer.

In some embodiments, the calculated signal ratios indicate that the DNA is lung cancer DNA.

A person of skill in the art would appreciate that the comparison of signal ratios calculated for a tested sample to corresponding reference signal ratios may be performed in a number of ways, using various statistical means.

In some embodiments, comparing a test signal ratio calculated for a given pair of loci to a reference signal ratio comprises comparing the test signal ratio against a single reference value. The single reference value may correspond to a mean value obtained for reference signal ratios from a large population of cancer patients or healthy individuals. In other embodiments, comparing a test signal ratio calculated for a given pair of loci to a reference signal ratio comprises comparing the test signal ratio against a distribution, or scale, of a plurality of reference signal ratios.

Known statistical means may be employed in order to determine whether the signal ratio calculated between a given restriction locus and a control locus corresponds to lung cancer reference ratio or to normal reference ratio. In some embodiments, detecting close approximation of a calculated ratio to lung cancer reference ratio identifies a subject as a subject having lung cancer. Conversely, in some embodiments, detecting close approximation of a calculated ratio to normal reference ratio identifies a subject as a subject not having lung cancer.

The method of the present invention is based on analyzing whether a signal ratio of a tested DNA sample is a lung cancer ratio, namely, indicative of lung cancer. In some embodiments, the method comprises comparing a calculated signal ratio to its corresponding healthy reference ratio (i.e., to a signal ratio determined for the same pair of loci in healthy subjects) to obtain a score (probability score) reflecting the likelihood that the calculated signal ratio is a lung cancer ratio. In some embodiments, the method comprises comparing a calculated signal ratio to its corresponding lung cancer reference ratio (i.e., to a signal ratio determined for the same pair of loci in lung cancer) to obtain a score reflecting the likelihood that the calculated signal ratio is a lung cancer ratio. The better approximation of the calculated signal ratio to the lung cancer reference ratio, the higher the score (probability score) and accordingly the likelihood that the calculated signal ratio is a lung cancer ratio. In some embodiments, the probability score is based on the relative position of the calculated signal ratio within the distribution of lung cancer reference ratios.

In some embodiments, the method comprises comparing a plurality of signal ratios, calculated for a plurality of restriction loci with respect to a control locus, to their corresponding healthy and/or lung cancer references ratios.

In some embodiments, a pattern of signal ratios may be analyzed using statistical means and computerized algorithm to determine if it represents a pattern of lung cancer or a normal, healthy pattern. Exemplary algorithms are disclosed, for example, in WO 2011/070441, assigned to the Applicant of the present invention. The algorithms may include, but are not limited to, machine learning and pattern recognition algorithms In some exemplary embodiments, each calculated ratio (for each pair of restriction and control locus) may be compared against a scale of reference ratios generated for this pair from a large set of plasma samples from cancer patients, individuals not afflicted with cancer, or both. The scale may represent signal ratios calculated between the pair of restriction locus and control locus in a large number of samples from cancer patients and/or normal individuals. The scale may exhibit a threshold value, also termed hereinafter 'cutoff' or 'pre-defined threshold', above which are reference ratios corresponding to lung cancer and below are reference ratios corresponding to healthy individuals, or the other way around.

In some embodiments, the lower ratios, at the bottom of the scale and/or below a cutoff, may be from samples of normal individuals (healthy, i.e., not afflicted with lung cancer), while the higher ratios at the top of the scale and/or above a predetermined cutoff, may be from the cancer patients. For each ratio (between each restriction locus and the control locus), a score may be given based on its relative position within the scale, and the individual scores (for each locus) are combined to give a single score. In some embodiments, the individual scores may be summed to give a single score. In other embodiments, the individual scores may be averaged to give a single score. In some embodiments, the single score may be used for determining whether the subject is having cancer, where a score above a pre-defined threshold is indicative of lung cancer.

In some embodiments, a score is a number between 0-100 reflecting the probability that the calculated signal ratio is a lung cancer ratio, wherein 0 being the lowest probability and 100 being the highest probability. In some embodiments, a threshold score is determined, wherein a score equal to or above which is indicative of lung cancer. The threshold may be, for example, 60, 70 or 80. Each possibility represents a separate embodiment of the present invention.

In additional exemplary embodiments, for each calculated ratio (between each restriction locus and the control locus), the probability that it represents lung cancer DNA may be determined based on comparison to corresponding lung cancer reference ratio and/or normal reference ratio, and a score (probability score) may be allocated. Consequently, the individual probability scores calculated for each ratio (for each locus) are combined (e.g. summed or averaged) to give a combined score. The combined score may be used for determining whether the subject is having cancer, where a combined score above a pre-defined threshold is indicative of lung cancer.

Thus, in some embodiments, a threshold, or cutoff, score is determined, above (or below) which the subject is identified as having lung cancer. The threshold score differentiates the population of healthy subjects from the population of non-healthy subject.

In some embodiments, the method of the present invention comprises providing a threshold score.

In some embodiments, determining the threshold score includes measuring signal ratios in a large population of subjects that are either healthy or have lung cancer.

In some embodiments, the threshold values are statistically significant values. Statistical significance is often determined by comparing two or more populations, and determining a confidence interval (CI) and/or a p value. In some embodiments, the statistically significant values refer to confidence intervals (CI) of about 90%, 95%, 97.5%, 98%, 99%, 99.5%, 99.9% and 99.99%, while preferred p values are less than about 0.1, 0.05, 0.025, 0.02, 0.01, 0.005, 0.001 or less than 0.0001. Each possibility represents a separate embodiment of the present invention. According to some embodiments, the p value of the threshold score is at most 0.05.

As used herein, the term "about", when referring to a measurable value is meant to encompass variations of +/−10%, more preferably +/−5%, even more preferably +/−1%, and still more preferably +/−0.1% from the specified value.

In some embodiments, the method further comprises comparing the signal ratio calculated between a given restriction locus and a control locus to its corresponding normal/healthy reference ratio to obtain a probability score, wherein detecting a low probability score for said ratio with respect to the corresponding healthy reference ratio is indicative that the subject has lung cancer.

In some embodiments, the sensitivity of the methods disclosed herein may be at least about 75%. In some embodiments, the sensitivity of the methods may be at least about 80%. In some embodiments, the sensitivity of the method may be at least about 85%. In some embodiments, the sensitivity of the methods may be at least about 90%.

In some embodiments, the "sensitivity" of a diagnostic assay as used herein refers to the percentage of diseased individuals who test positive (percent of "true positives"). Accordingly, diseased individuals not detected by the assay are "false negatives". Subjects who are not diseased and who test negative in the assay are termed "true negatives." The "specificity" of the diagnostic assay is one (1) minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

In some embodiments, the specificity of the methods disclosed herein may be at least about 65%. In some embodiments, the specificity of the methods may be at least about 70%. In some embodiments, the specificity of the method may be at least about 75%. In some embodiments, the specificity of the methods may be at least about 80%.

Definitive Diagnosis of Lung Cancer

In some embodiments, following identification of lung cancer in a human subject according to the method of the present invention, the subject may undergo definitive diagnosis of lung cancer. The definitive diagnosis of lung cancer is based on histological examination of a suspicious lung tissue following biopsy. The procedure typically involves bronchoscopy or CT-guided biopsy to sample the suspicious lung tissue.

Lung Cancer Treatment

In some embodiments, methods for treating lung cancer are provided, comprising identifying lung cancer according to the method of the present invention, and administering to said subject anti-lung cancer therapy.

Methods for treating lung cancer may include one or more of: surgery to remove the tumor, radiofrequency ablation (RFA), radiation therapy, chemotherapy, targeted therapies and immunotherapy, as known in the art. Each possibility represents a separate embodiment of the present invention.

Kits and Systems

In some embodiments, there is provided a kit for identification of lung cancer in a human subject. In some embodiments, there is provided a system for identification of lung cancer in a human subject.

In some embodiments, the kit and system are for identification of lung cancer according to the method of the present invention.

In some embodiments, the kit comprises at least one methylation-sensitive restriction enzyme for digesting DNA from a plasma sample from a human subject and a plurality of primer pairs for co-amplification of at least one restriction locus and at least one control locus following digestion with the at least one methylation-sensitive restriction enzyme, wherein the at least one restriction locus is selected from the group consisting of SEQ ID NO: 1, SEQ ID NO: 2, SEQ ID NO: 3, SEQ ID NO: 4, SEQ ID NO: 5 and SEQ ID NO: 6.

In some embodiments, the kit further comprises a plurality of polynucleotide probes for detecting amplification products of the at least one restriction locus and the at least one control locus.

In some embodiments, the kit further comprises instructions for carrying out the identification of lung cancer using a computer software stored on a computer-readable medium, the computer software directs a computer processor to perform the following steps: determining signal intensities for the at least one restriction locus and the control locus following their amplification; calculating signal ratios between the signal intensities of each of the at least one restriction locus and the control locus; comparing the calculated signal ratios to at least one reference ratio; and based on the comparison, outputting whether the DNA sample is lung cancer DNA or healthy DNA In some embodiments, the kit further comprises a computer readable medium storing a computer software that directs a computer processor to perform the following steps: determining signal intensities for the at least one restriction locus and the control locus following their amplification; calculating signal ratios between the signal intensities of each of the at least one restriction locus and the control locus; comparing the calculated signal ratios to at least one reference ratio; and based on the comparison, outputting whether the DNA sample is lung cancer DNA or healthy DNA.

In some embodiments, the system comprises: at least one methylation-sensitive restriction endonuclease for digesting DNA from a plasma sample from a human subject; a plurality of primer pairs for co-amplification of at least one restriction locus and at least one control locus following digestion with the at least one methylation-sensitive restriction enzyme, wherein the at least one restriction locus is selected from the group consisting of SEQ ID NO: 1, SEQ ID NO: 2, SEQ ID NO: 3, SEQ ID NO: 4, SEQ ID NO: 5 and SEQ ID NO: 6; and computer software stored on a computer readable medium, the computer software directs a computer processor to perform the following steps: determining signal intensities for the at least one restriction locus and the control locus following their amplification; calculating signal ratios between the signal intensities of each of the at least one restriction locus and the control locus; comparing the calculated signal ratios to at least one reference ratio; and based on the comparison, outputting whether the DNA sample is lung cancer DNA or healthy DNA.

In some embodiments, a computer software according to the present invention receives as an input parameters or raw data of a real-time PCR run. In some embodiments, the computer software directs a computer processor to analyze the real-time PCR run to determine signal intensities and signal ratios.

The computer software includes processor-executable instructions that are stored on a non-transitory computer readable medium. The computer software may also include stored data. The computer readable medium is a tangible computer readable medium, such as a compact disc (CD), magnetic storage, optical storage, random access memory (RAM), read only memory (ROM), or any other tangible medium.

In some embodiments, the kit comprises at least one methylation-sensitive restriction enzyme; pairs of primers for amplification of at least one restriction locus and at least one control locus; means for detecting amplification products of the at least one restriction locus and at least one control locus; and instruction manual for carrying out the identification of lung cancer. In some embodiments, the instruction manual may be an electronic instruction manual.

In some embodiments, the instruction manual may provide lung cancer reference ratios and/or healthy reference ratios.

In some embodiments, the instruction manual may include instructions for performing the method steps described above.

In some embodiments, the instruction manual may include instructions directing the correlation between signal ratio(s) and lung cancer reference ratio(s) and/or healthy reference ratio(s).

In some embodiments, the instruction manual may provide instructions for calculating a probability score for a given restriction locus. In some embodiments, the instruction manual may provide instructions for calculating a total score for a plurality of probability scores. In some embodiments, the instruction manual may provide a threshold score for determining lung cancer, above which a subject is identified as having lung cancer. In other embodiments, the instruction manual may provide a threshold score for determining lung cancer, below which a subject is identified as having lung cancer.

In some embodiments, the kit comprises a single methylation-sensitive endonuclease. In some embodiments, the methylation-sensitive endonuclease is HinP1I. In additional embodiments, the methylation-sensitive endonuclease is HhaI.

In some embodiments, the kit may further comprise a computer software stored on computer readable medium. In some embodiments, the computer software may be a computer software that directs a computer processor to calculate at least one of signal intensities, signal ratios and probability scores according to the methods disclosed herein, and output whether a given DNA sample is a lung cancer DNA sample or a healthy DNA sample.

In some embodiments, the kit comprises: HinP1I or HhaI; primer pairs complementary to at least one restriction locus and at least one control locus as described herein; and fluorescent polynucleotide probes complementary to the at least one restriction locus and at least one control locus.

Exemplary primers for amplifying the restriction loci set forth in SEQ ID NOs: 1-6 are set forth in SEQ ID NOs: 8-79, as follows:

```
Locus 1
                                  (SEQ ID NO: 1)
Primers forward:
                                  (SEQ ID NO: 8)
TGCATTCTCTCAGGAGCTGG

                                  (SEQ ID NO: 9)
GAGCCAAGCTCGGTCTCCG

                                 (SEQ ID NO: 10)
CAGCAACGCTTTTGCCAGTAG

                                 (SEQ ID NO: 11)
TCTAATGCGGAGCTGGCGGT

                                 (SEQ ID NO: 12)
CCCACTGAGCGGTTTTTCAGT

                                 (SEQ ID NO: 13)
CGTTTCCCGTACGCGGAGTC
Primers reverse:
                                 (SEQ ID NO: 14)
GTTTTAATGTGTTGTGACAG

                                 (SEQ ID NO: 15)
GTGCTGCTAGAAAGAAACTG

                                 (SEQ ID NO: 16)
GGGTTTAGGAAGTTCCTAGGA

                                 (SEQ ID NO: 17)
TACTAGTTGGCACAGAGGCT
```

-continued

```
                                 (SEQ ID NO: 18)
CGGTGCCAGAACCGAGAAAG

                                 (SEQ ID NO: 19)
ACCGTTCTGCACCGTAAAAC
Locus 2
                                  (SEQ ID NO: 2)
Primers forward:
                                 (SEQ ID NO: 20)
CGGAATAGGGTTTGCAAATC

                                 (SEQ ID NO: 21)
AGGAGATGCTGCTTGTTCGG

                                 (SEQ ID NO: 22)
GTTGAAGCTTTTAATACATG

                                 (SEQ ID NO: 23)
ACAGCTCACGGTCCCGCAG

                                 (SEQ ID NO: 24)
GCCCGCCACACACCCGC

                                 (SEQ ID NO: 25)
CTTGAGATGAGGTTCCCAAGC
Primers reverse:
                                 (SEQ ID NO: 26)
AGATGAGTAGCGAGCCTTGTC

                                 (SEQ ID NO: 27)
CGTGCTTTGCCGATCGAATTC

                                 (SEQ ID NO: 28)
TTCCTGCTCGAGTCCACTCG

                                 (SEQ ID NO: 29)
CGGGTGTATCTTCCTGCTCGA

                                 (SEQ ID NO: 30)
CGAGCCTTGACGGAGGGAGA

                                 (SEQ ID NO: 31)
CGGAGGGAGAATGGAAAGAT
Locus 3
                                  (SEQ ID NO: 3)
Primers forward:
                                 (SEQ ID NO: 32)
TTTCCTCCGCCACCGAGTAG

                                 (SEQ ID NO: 33)
GAAGTTTAAGTTTCCAGGTCC

                                 (SEQ ID NO: 34)
ATTTGCGAAGTTTAAGTTTCC

                                 (SEQ ID NO: 35)
AGCAGCCAGGGATCGGATAG

                                 (SEQ ID NO: 36)
TCGGCAGCCGCCCTGGTAGC

                                 (SEQ ID NO: 37)
CCCCATTTGCGAAGTTTAAG
Primers reverse:
                                 (SEQ ID NO: 38)
GGCAGTCTAATCCTTAATTT

                                 (SEQ ID NO: 39)
ATTTTAATAATCAGGATAAA

                                 (SEQ ID NO: 40)
ATGTTCGAGTCGGTCGTAACG

                                 (SEQ ID NO: 41)
GTACACAAACGAATACTAGCTAA
```

(SEQ ID NO: 42)
CTAGGCAGTCTAATCCTTAAT (SEQ ID NO: 43)
ATACTAGCTAAGGCCGATGAT

Locus 4

(SEQ ID NO: 4)

Primers forward:

(SEQ ID NO: 44)
CTCTCTGCTGTAGCGACGCCA (SEQ ID NO: 45)
GCTTTCCGCCGGGTAAATTAG (SEQ ID NO: 46)
TTTGGTTATAGTGGTGTGGTCT (SEQ ID NO: 47)
CCACCCCATCTTCGCAGTTCT (SEQ ID NO: 48)
TCCTCCTTGCCTTCTTTCGC (SEQ ID NO: 49)
ATAGTGGTGTGGTCTCTGCCTC

Primers reverse:

(SEQ ID NO: 50)
GTTTTGTTACTGTCTGTCCT (SEQ ID NO: 51)
TCCTGCCAGGTGTCTACATGT (SEQ ID NO: 52)
ACTGTCTGTCCTGCAGGAACCC (SEQ ID NO: 53)
TGAAGGCAGGATAGGTACCAG (SEQ ID NO: 54)
TCAAACTATTATTTCCCACGTT (SEQ ID NO: 55)
ACATGTTTCCATTAAGATGC

Locus 5

(SEQ ID NO: 5)

Primers forward:

(SEQ ID NO: 56)
CCTGACGTTCCTGGAATATGC (SEQ ID NO: 57)
GCAATGACTTCTTTTAGGACA (SEQ ID NO: 58)
TGAAAGCAGCATTAACCGTG (SEQ ID NO: 59)
AGGACCCGCTCCGCAAAGC (SEQ ID NO: 60)
ACCCTCGAGGGAGGAAAGCC (SEQ ID NO: 61)
AACCCGTTACTTTCCAAGGAC

Primers reverse:

(SEQ ID NO: 62)
GCCACACTCCCTGGCCTTG (SEQ ID NO: 63)
GCGGGGCTCGAGCCACACT (SEQ ID NO: 64)
CCTCCGCACTGGGAGGCTG (SEQ ID NO: 65)
TCGCAGCCGAGGCAGGTCT (SEQ ID NO: 66)
CCCGACAGTGTCATTGATTAAC (SEQ ID NO: 67)
CCTCCGCAGCTGGGAGGCTG

Locus 6

(SEQ ID NO: 6)

Primers forward:

(SEQ ID NO: 68)
CTCGGGGACTGCTACTTTGC (SEQ ID NO: 69)
GGTCAAGTGTCACGTCCTCC (SEQ ID NO: 70)
ATATTCCTGTAATGTATTTAAAT (SEQ ID NO: 71)
TACGCGGGGCCGTGTGAAT (SEQ ID NO: 72)
GGTCAAGTGTCACGTCCTCC (SEQ ID NO: 73)
AAGTGTCACGTCCTCCGCAA

Primers reverse:

(SEQ ID NO: 74)
GCGAGGACGCAAACACCATT (SEQ ID NO: 75)
CCTAAAGGACCCTACCAAGC (SEQ ID NO: 76)
GTGCCTGAACTCTTCCTCCTT (SEQ ID NO: 77)
TTCCGTGGGTCCGCGGTCT (SEQ ID NO: 78)
ATCAGAAAGACCATTAGGATC (SEQ ID NO: 79)
CCGAAGGGAAAGAAAAATCAG

Exemplary primers for amplifying the control locus set forth in SEQ ID NO: 7 are set forth in SEQ ID NOs: 80-91 as follows:

Control locus (SEQ ID NO: 7)

Primers forward:

(SEQ ID NO: 80)
AGCAAGGTGAAGACTAACTTTTC (SEQ ID NO: 81)
CTTGTACAGAATCATCAGGCTAA (SEQ ID NO: 82)
GTCCTTGGAGACATCTGAGAGATTC (SEQ ID NO: 83)
GACATCTGAGAGATTCCGGG (SEQ ID NO: 84)
CAAAGAAAGCAAGGTGAAGACT (SEQ ID NO: 85)
CAGTCCTTGGAGACATCTGAGAGA

-continued

```
Primers reverse:
                                          (SEQ ID NO: 86)
TGAAGTGAACTATTCCTTAGGTG

                                          (SEQ ID NO: 87)
GTCTCCAAGGACTGAAATAATGC

                                          (SEQ ID NO: 88)
GAGTAGCAAAAAATAGCTGAAGTGAACT

                                          (SEQ ID NO: 89)
TGACAACCAATGAGTAGCAAAAA

                                          (SEQ ID NO: 90)
GTTGTCAGTGTGGCCAGAGA

                                          (SEQ ID NO: 91)
TGTTGTCAGTGTGGCCAGAGA
```

In some embodiments, the kit comprises at least one of a first control construct and a second control construct, each comprising human cell line DNA as described above. In some embodiments, the kit comprises both first and second control DNA as described above.

In some embodiments, the kit comprises one or more containers filled with at least one nucleotide primer pair. In some embodiments, each nucleotide primer pair included in the kit of the present invention may include primers designed to selectively amplify a fragment of the genome that includes a restriction locus selected from the restriction loci set forth in SEQ ID NOs: 1-6s.

In some embodiments, the kit may comprise primer pairs for selectively amplifying the combination of loci described above.

In some embodiments, the kit may further include oligonucleotide probes for detecting amplification products of the loci amplified using the primers in the kit. Each oligonucleotide probe may be complementary to a sub-sequence within a locus and may be capable of hybridizing thereto. In some embodiments, the oligonucleotide probes may be fluorescently-labeled.

In some embodiments, the kit may further include at least one additional ingredient needed for DNA extraction, DNA digestion, loci amplification and detection of amplification products, such as DNA polymerase and nucleotide mix.

In some embodiments, the kit may further include suitable reaction buffers for digestion and amplification, and a written protocol for performing lung cancer identification. The written protocol may comprise instructions for performing any of the steps disclosed herein, including but not limited to, DNA digestion parameters, PCR cycling parameters, signal ratio analysis, and comparison to reference ratios.

The following examples are presented in order to more fully illustrate certain embodiments of the invention. They should in no way, however, be construed as limiting the broad scope of the invention. One skilled in the art can readily devise many variations and modifications of the principles disclosed herein without departing from the scope of the invention.

EXAMPLES

Example 1—Genomic Loci for Detection of Lung Cancer

Six (6) human genomic loci were identified as having increased methylation in DNA from plasma of lung cancer patients compared to DNA from plasma of individuals without lung cancer or other lung diseases (Table 1 herein below, SEQ ID NOs: 1-6). These loci were found to enable distinguishing between DNA from plasma of lung cancer patients and that of normal individuals (not afflicted with lung cancer or other lung diseases).

TABLE 1

Genomic loci

| SEQ ID NO. | Nucleic acid sequence | Description* |
|---|---|---|
| 1 | AGTAGCGCCCACTGAGCGGTTTTTC AGTTGCTGCACCGTTCTTAGCGCCC AACGGAACGTTTCCCGTACGCGGAG TCCATAAGTT | Position 43030476 on Chromosome 5, intergenic region |
| 2 | CGGTCCCGCA GCGCCCGCCA CACACCCGCG CCAGAGGTCC AGCGCATGTG CAGTGAAATG GCCTAGCCC | Position 176712760 on Chromosome 2, intergenic region |
| 3 | CGGATAGCGC GGCGGGCGAC AGCCCCCCGG ATAACCCCGC CGAGGGAGGG GCGCTTGTAA AACCGAGCGG CG | Position 44151837 on Chromosome 17, intergenic region |
| 4 | TCCTCCTTGC CTTCTTTCGC CGAAAGGGGG CGCGCTCCTC CCAGGCTGCG CTGGTACCTA | Position 168907269 on Chromosome 1, PRRX1 gene |
| 5 | AGGACCCGCT CCGCAAAGCG CCCACCCTCG AGGGAGGAAA GCCGAGCTGC GCCTCCGCGC AAGGCCAGGG AGTGTGGC | Position 158629293 on Chromosome 7, VIPR2 gene |
| 6 | AGGCCGCGAG CGCGGCGCGA TCAGTAGCGC CCACTAACAG TTCGTTCTGC ACGGCGGAGC GCGAGACCGC GGA | Position 154860262 on Chromosome 7, intergenic region |

TABLE 1-continued

| Genomic loci | | |
|---|---|---|
| SEQ ID NO. | Nucleic acid sequence | Description* |
| 7 | AGACTAACTTTTCTCTTGTACAGAAT CATCAGGCTAAATTTTTGGCATTATT TCAGTCCT | Position 121380854-121380913 on Chromosome 7, intergenic region |

*The description refers to position on hg18 genomic build

Example 2—Testing the Panel of Genomic Loci

Plasma samples were obtained from 133 lung cancer patients and from 121 healthy subjects not afflicted with lung cancer, over the age of 50, who are current or past smokers. Of the lung cancer patient population, 49 had squamous cell carcinoma, 50 had adenocarcinoma, 2 had mixed non-small cell lung cancers, and 4 had other types of non-small cell lung cancers. 11 patients had small cell lung cancer, and further 17 patients had lung cancer with unknown histological type. In the non-small cell lung cancer population, 18 patients had stage I disease, 17 patients had stage II disease, 49 patients had stage III disease, 32 patients had stage IV disease, and for 6 patients the stage was unknown. In the small cell lung cancer population, 4 patients had limited disease and 7 had extensive disease.

Figure 2:
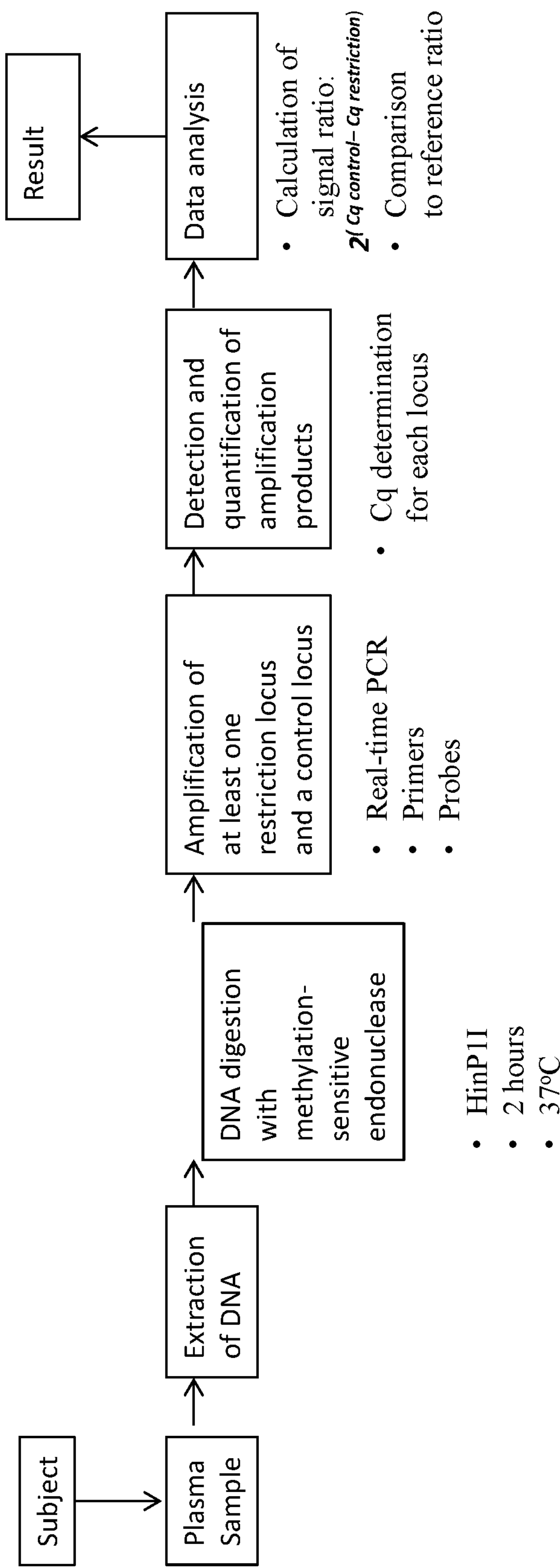
FIG. 2 is a flow-chart describing a method for identifying lung cancer in a subject according to some embodiments of the present invention.

DNA was extracted from the plasma samples using the QIAamp® Circulating Nucleic Acid Kit (QIAGEN, Hilden, Germany). The extracted DNA from each sample was processed as outlined in FIG. 2. In brief, the extracted DNA was subjected to digestion with the methylation-sensitive restriction endonuclease HinP1I. The digestion reaction (total volume 100 microliter) included 80 microliters of the extracted DNA (not quantified) and HinP1I in a digestion buffer. The digestion was carried out at 37° C. for 2 hours.

Next, real-time PCR was carried out on the digested DNA samples to amplify in each DNA sample the 6 restriction loci detailed in Table 1 above and a control locus as set forth in SEQ ID NO: 7 (see Table 1). The control locus is a locus that does not contain a recognition sequence of HinP1I and remains intact when a DNA sample is digested with the restriction enzyme regardless of its methylation status. This control locus, also termed an internal reference locus, has an amplification pattern which following digestion with HinP1I is not affected by methylation.

In particular, each digested DNA sample was divided into three (3) aliquots containing 12 microliters of the digested DNA. Each aliquot was supplemented with primer pairs for amplification of two restriction loci out of the six and the control locus (the control locus is to be amplified in every aliquot). Amplicons of between 77 to 139 bases were amplified.

Each amplification reaction (total volume 30 microliter) further contained dNTPs and a reaction buffer. To enable detection of amplification products during amplification, fluorescently-labeled polynucleotide probes (one for each locus) were added to the reaction. The following fluorescent labels were used: FAM, JOE, ROX. Real-time PCR reactions were carried out in an ABI 7500 FastDx instrument with the following PCR program: 95° C., 10 min→45×(95° C., 15 sec)→60° C., 1 min.

Following amplification, data on the level of fluorescent signals from the probes as a function of cycle number were analyzed to calculate the quantification cycle (Cq) for each locus and the ΔCq (difference between the Cq of the restriction locus and the Cq of the control locus) of each restriction locus.

Figure 1B:
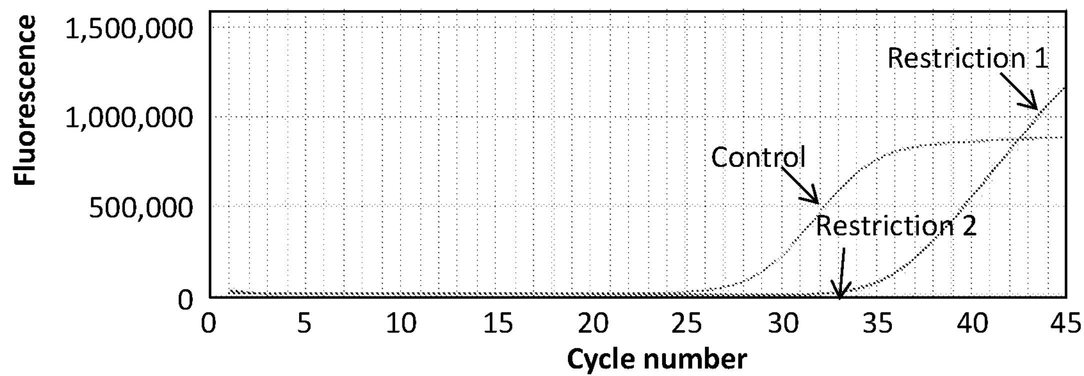
FIG. 1B exhibits exemplary amplification plots of a control locus and two restriction loci in a sample from a lung cancer patient.

FIGS. 1A and 1B show exemplary quantitative PCR plots of the control locus and two restriction loci in a sample from a cancer patient (FIG. 1A) and in a sample from a healthy subject (FIG. 1B). In the sample from a cancer patient, in which the restriction loci have high methylation levels and therefore remained mostly intact when digested with HinP1I, the two restriction loci were amplified with high efficiency, i.e. the difference between their Cq and the Cq of the control locus (ΔCq) was about 3 cycle(s). In the healthy sample, in which the restriction loci are characterized with low methylation levels and were therefore cut extensively when digested with HinP1I, the efficiency of amplification was much lower than the efficiency of amplification of the control locus, reflected by high ΔCq with respect to the control locus. As can be taken from the figures, the ΔCq values of the restriction loci with respect to the control locus differ between cancer patients and healthy subjects.

For each sample, ratios were calculated between the signal intensity of each of restriction loci 1-6 (SEQ ID NO: 1-6) and the signal intensity of the control locus (SEQ ID NO: 7), as follows: the Cq was determined for each restriction locus and for the control locus. The Cq values were used in the following formula:

$$2^{(Cq\ of\ control\ locus - Cq\ of\ restriction\ locus)}$$

It is to be understood that the calculation was performed for a restriction locus and a control locus that were co-amplified in the same aliquot.

The numerical value obtained for each restriction locus with respect to the control locus represents the signal ratio (reflecting methylation ratio) between this restriction locus and the control locus.

Altogether, six signal ratios were calculated for each sample. Table 2 lists exemplary signal ratios calculated for 10 plasma samples from healthy subjects and 10 samples from lung cancer patients. As can be seen from the table, signal ratios calculated for cancer samples are significantly higher than the signal ratios calculated for healthy samples (up to several orders of magnitude higher).

Next, a score (probability score) was calculated for each locus in each sample, the score being the signal ratio normalized in respect to reference ratios such that the highest signal ratio is scored "100" and the lowest signal ratio is scored "0".

Next, the six scores obtained for each sample were combined into a single score, termed "EpiScore", which is a number between 0 and 100, reflecting the overall relative methylation level of the sample at the panel of six restriction loci.

Table 2 lists exemplary signal ratios and EpiScores, showing that higher EpiScores correlate with lung cancer ($P=2.44 \cdot 10^{-25}$ according to the Kolmogorov-Smirnov goodness of fit hypothesis test, for the entire set of samples), highlighting the advantage of using the method of the present invention in differentiating between plasma samples of lung cancer patients and those of normal/healthy individuals.

A sample was classified as "lung cancer" if its EpiScore was above or equal to 70 (a threshold that was determined based on information from an earlier set of samples), and as "healthy" if its EpiScore was below 70.

TABLE 2

| | signal ratios | | | | | | | |
|---|---|---|---|---|---|---|---|---|
| | Sam- | Locus | | | | | | Epi- |
| | ple | 1 | 2 | 3 | 4 | 5 | 6 | Score |
| healthy | 1 | 1:5739 | 1:158 | 1:315 | 1:16384 | 1:338 | 1:16384 | 29 |
| | 2 | 1:16384 | 1:119 | 1:388 | 1:16384 | 1:388 | 1:16384 | 25 |
| | 3 | 1:16384 | 1:181 | 1:315 | 1:891 | 1:549 | 1:16384 | 30 |
| | 4 | 1:16384 | 1:158 | 1:388 | 1:676 | 1:119 | 1:16384 | 39 |
| | 5 | 1:588 | 1:119 | 1:239 | 1:16384 | 1:34 | 1:16384 | 53 |
| | 6 | 1:16384 | 1:119 | 1:724 | 1:181 | 1:294 | 1:16384 | 38 |
| | 7 | 1:16384 | 1:69 | 1:239 | 1:16384 | 1:388 | 1:16384 | 36 |
| | 8 | 1:3566 | 1:208 | 1:208 | 1:16384 | 1:158 | 1:724 | 46 |
| | 9 | 1:1663 | 1:74 | 1:549 | 1:16384 | 1:137 | 1:16384 | 45 |
| | 10 | 1:16384 | 1:128 | 1:169 | 1:5405 | 1:119 | 1:1351 | 49 |
| cancer | 1 | 1:2.5 | 1:1.2 | 1:1.6 | 1:2 | 1:43 | 1:22 | 99 |
| | 2 | 1:34 | 1:20 | 1:90 | 1:181 | 1:17 | 1:43 | 98 |
| | 3 | 1:5 | 1:6.5 | 1:3 | 1:6 | 1:4 | 1:1663 | 95 |
| | 4 | 1:104 | 1:14 | 1:14 | 1:30 | 1:12 | 1:97 | 100 |
| | 5 | 1:39 | 1:10.6 | 1:6 | 1:9 | 1:4 | 1:30 | 100 |
| | 6 | 1:26 | 1:12 | 1:23 | 1:21 | 1:18 | 1:42 | 100 |
| | 7 | 1:6 | 1:4 | 1:7 | 1:5 | 1:3 | 1:4 | 100 |
| | 8 | 1:12 | 1:6.5 | 1:2.6 | 1:4 | 1:6 | 1:4 | 100 |

TABLE 2-continued

| signal ratios | | | | | | | |
|---|---|---|---|---|---|---|---|
| Sam- | Locus | | | | | | Epi- |
| ple | 1 | 2 | 3 | 4 | 5 | 6 | Score |
| 9 | 1:13 | 1:14 | 1:9 | 1:158 | 1:15 | 1:17 | 100 |
| 10 | 1:30 | 1:34 | 1:40 | 1:28 | 1:64 | 1:37 | 98 |

Sensitivity, specificity and area under an ROC curve (AUC) with respect to identification of lung cancer were calculated for the locus set forth in SEQ ID NO: 4 and for the combinations of loci 1-6. The data is summarized in Table 3.

TABLE 3

| Sensitivity, specificity and AUC | | | |
|---|---|---|---|
| Loci (SEQ ID NO) | Sensitivity | Specificity | AUC |
| 4 | 52.6% | 90% | 0.783 |
| All (1-6) | 74.4% | 90.9% | 0.873 |

The foregoing description of the specific embodiments will so fully reveal the general nature of the invention that others can, by applying current knowledge, readily modify and/or adapt for various applications such specific embodiments without undue experimentation and without departing from the generic concept, and therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed chemical structures and functions may take a variety of alternative forms without departing from the invention.

What is claimed is:

1. A method for measuring methylation ratio of DNA present in a plasma sample from a human subject suspected of having lung cancer, the method comprising:

(a) subjecting DNA from a plasma sample obtained from the subject to digestion with at least one methylation-sensitive restriction endonuclease, thereby obtaining restriction endonuclease-treated DNA;

(b) co-amplifying from the restriction endonuclease-treated DNA at least one restriction locus having increased methylation in lung cancer DNA compared to normal non-cancerous DNA and a control locus, wherein the at least one restriction locus is selected from the group consisting of SEQ ID NO: 1, SEQ ID NO: 2, SEQ ID NO: 3, SEQ ID NO: 4, SEQ ID NO: 5, and SEQ ID NO: 6, and wherein the control locus is a locus in the restriction endonuclease-treated DNA that is not cut by the methylation-sensitive restriction enzyme used in the digestion step, thereby generating at least one restriction locus amplification product, and a control locus amplification product;

(c) determining a signal intensity for each generated restriction locus amplification product, wherein the signal intensity is indicative of a methylation level of CpG sites within the corresponding restriction locus, and determining a signal intensity for the control locus amplification product; and (d) calculating a ratio between the signal intensities of the amplification products of each of said at least one restriction locus and the control locus, thereby measuring methylation ratio of DNA in the plasma sample.

2. The method of claim 1, wherein step (a) is performed using a single methylation-sensitive restriction endonuclease selected from HinP1I and HhaI.

3. The method of claim 1, wherein step (b) is performed using real-time PCR.

4. The method of claim 3, wherein the method further comprises adding fluorescent probes for assisting in detecting the amplification products of the at least one restriction locus and the control locus, and wherein the ratio between the signal intensities of the amplification products of each of said at least one restriction locus and the control locus is calculated by determining the quantification cycle (Cq) for each locus and calculating 2(Cq control locus−Cq restriction locus).

5. The method of claim 1, wherein the at least one restriction locus comprises the locus set forth in SEQ ID NO: 4, and optionally at least one additional restriction locus selected from the group of loci set forth in SEQ ID NO: 1, SEQ ID NO: 2, SEQ ID NO: 3, SEQ ID NO: 5, and SEQ ID NO: 6.

6. The method of claim 1, wherein the at least one restriction locus comprises all loci set forth in SEQ ID NO: 1, SEQ ID NO: 2, SEQ ID NO: 3, SEQ ID NO: 5, and SEQ ID NO: 6.

7. The method of claim 1, further comprising:

providing first and second control DNA, each comprising human cell line-derived DNA, wherein the first control DNA comprises DNA from a human cell line in which the at least one restriction locus is at least 75% methylated, and the second control DNA comprises DNA from a human cell line in which one or more of the at least one restriction locus is at least 75% unmethylated;

digesting the first and second control DNA with the methylation-sensitive restriction endonuclease to provide a first digested control DNA and a second digested control DNA; and amplifying the first digested control DNA and second digested control DNA to provide a first control DNA amplification product and a second control DNA amplification product;

generating a separate fluorescent signal from each of the at least one restriction locus amplification product, the control locus amplification product, the first control DNA amplification product, and the second control DNA amplification product, wherein each separate fluorescent signal correlates with the amount of the corresponding amplification product and adequate amplification is defined as a fluorescence level above 100,000 units for each separate fluorescent signal, wherein detection of adequate amplification of the at least one restriction locus and the control locus in the first control DNA is indicative of successful DNA amplification, and wherein low or absence of amplification of one or more of the at least one restriction locus concomitant with normal amplification of the control locus in the second control DNA is indicative of successful DNA digestion.

8. The method of claim 1, wherein the control locus is the locus set forth in SEQ ID NO: 7.

9. A method of screening for lung cancer in a human subject, the method comprising:

measuring methylation ratio of DNA in a plasma sample from the human subject according to the method of claim 1; and determining that lung cancer is present in the human subject based on the methylation ratio.

* * * * *